US008986376B2

(12) United States Patent
Solem

(10) Patent No.: US 8,986,376 B2
(45) Date of Patent: Mar. 24, 2015

(54) DEVICE AND A METHOD FOR AUGMENTING HEART FUNCTION

(71) Applicant: Synergio AG, Schaffhausen (CH)

(72) Inventor: Jan Otto Solem, Bjärred (SE)

(73) Assignee: Synergio AG, Schaffhausen (CH)

(*) Notice: Subject to any disclaimer, the term of this patent is extended or adjusted under 35 U.S.C. 154(b) by 0 days.

(21) Appl. No.: 13/933,048

(22) Filed: Jul. 1, 2013

(65) Prior Publication Data

US 2013/0289717 A1    Oct. 31, 2013

Related U.S. Application Data

(63) Continuation of application No. 13/122,394, filed as application No. PCT/SE2011/050338 on Mar. 25, 2011.

(60) Provisional application No. 61/317,631, filed on Mar. 25, 2010.

(51) Int. Cl.
A61F 2/24 (2006.01)
A61M 1/10 (2006.01)

(52) U.S. Cl.
CPC .............. A61F 2/2409 (2013.01); A61F 2/2412 (2013.01); A61F 2/2436 (2013.01); A61F 2/2445 (2013.01); A61F 2210/009 (2013.01); A61M 1/1081 (2013.01); A61M 1/1087 (2014.02)
USPC .......... 623/3.11; 623/3.1; 623/1.26; 623/2.36; 623/2.37

(58) Field of Classification Search
USPC ................ 623/1.26, 2.36, 2.37, 3.1, 3.11
See application file for complete search history.

(56) References Cited

U.S. PATENT DOCUMENTS

| 2002/0138138 A1 | 9/2002 | Yang |
| 2003/0225454 A1 | 12/2003 | Mathis et al. |
| 2006/0129025 A1 | 6/2006 | Levine et al. |
| 2007/0016288 A1 | 1/2007 | Gurskis et al. |

FOREIGN PATENT DOCUMENTS

| EP | 2072027 A1 | 6/2009 |
| WO | WO 2007/029252 A2 | 3/2007 |
| WO | WO 2009/134701 A2 | 11/2009 |
| WO | WO 2009/140298 A2 | 11/2009 |

OTHER PUBLICATIONS

WIPO, WIPO International Preliminary Examining Authority, International Preliminary Report on Patentability mailed Oct. 4, 2012 in International Patent Application No. PCT/SE2011/050338, 9 pages.
WIPO, Swedish International Search Authority, International Search Report and Written Opinion mailed Jun. 20, 2011 in International Patent Application No. PCT/SE2011/050338, 13 pages.

Primary Examiner — Randy Shay
Assistant Examiner — Dinah Baria
(74) Attorney, Agent, or Firm — Inskeep IP Group, Inc.

(57) ABSTRACT

A device, a kit and a method are presented for permanently augmenting the pump function of the left heart. The basis for the presented innovation is an augmentation of the physiologically up and down movement of the mitral valve during each heart cycle. By means of catheter technique, minimal surgery, or open heart surgery implants are inserted into the left ventricle, the mitral valve annulus, the left atrium and adjacent tissue in order to augment the natural up and down movement of the mitral valve and thereby increasing the left ventricular diastolic filling and the piston effect of the closed mitral valve when moving towards the apex of the heart in systole and/or away from the apex in diastole.

40 Claims, 18 Drawing Sheets

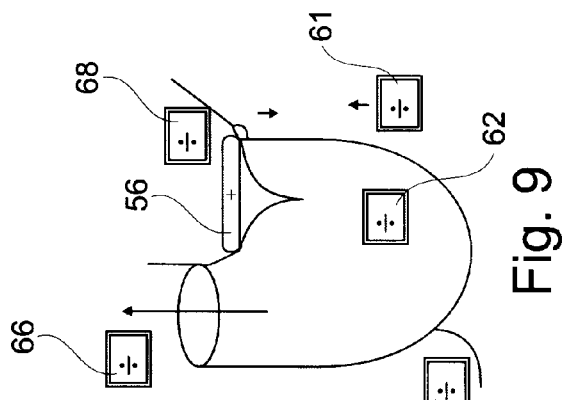
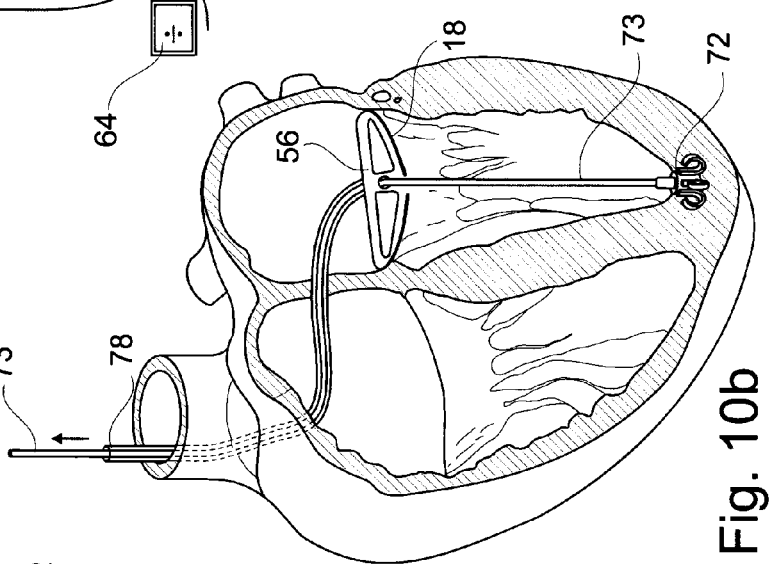
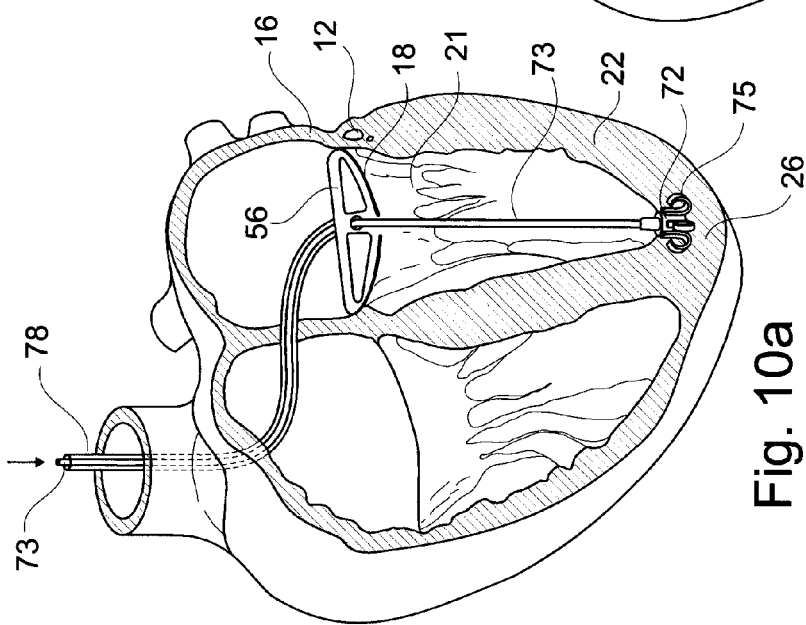

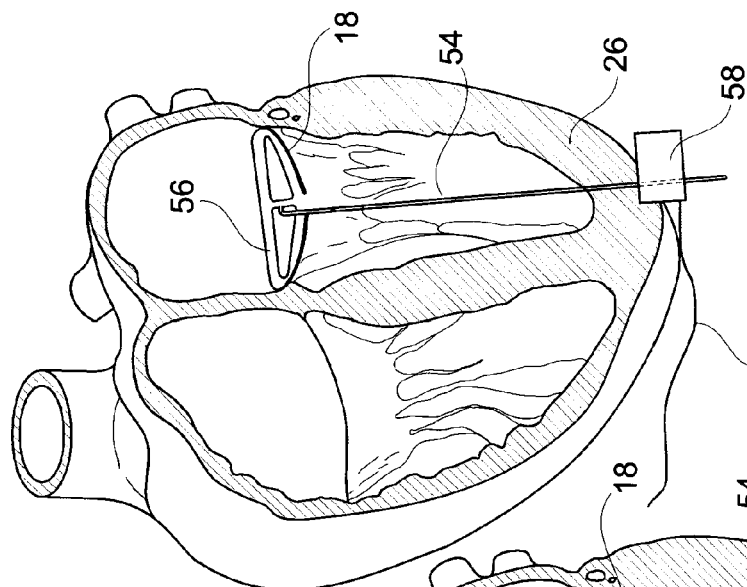
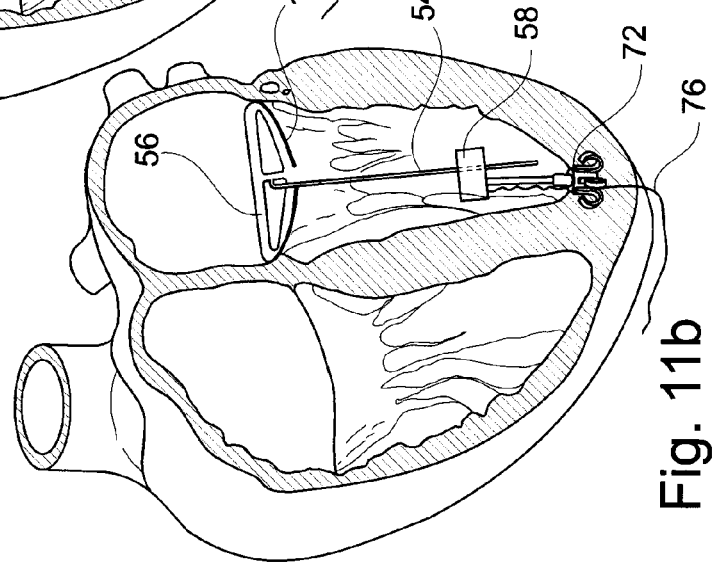
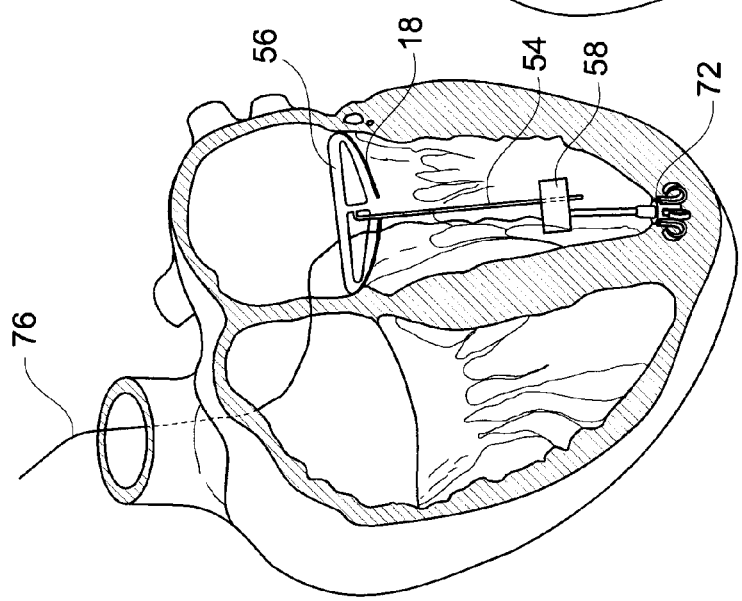

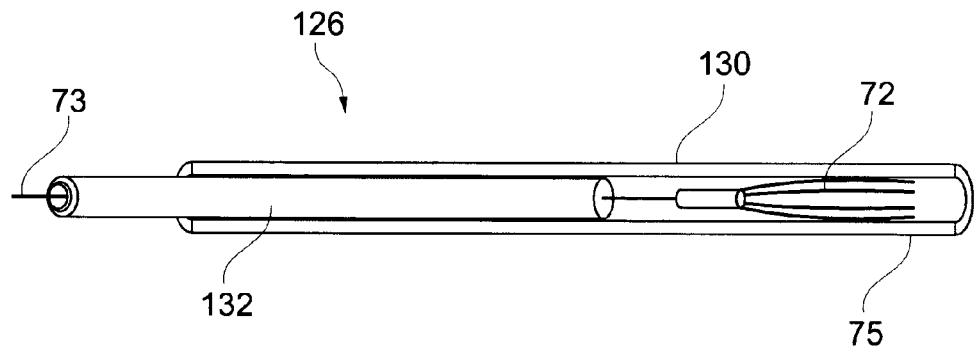
Fig. 23
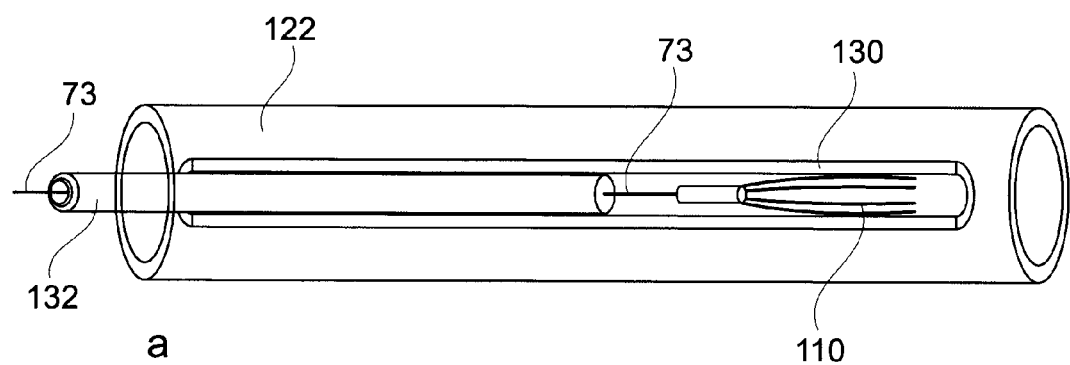
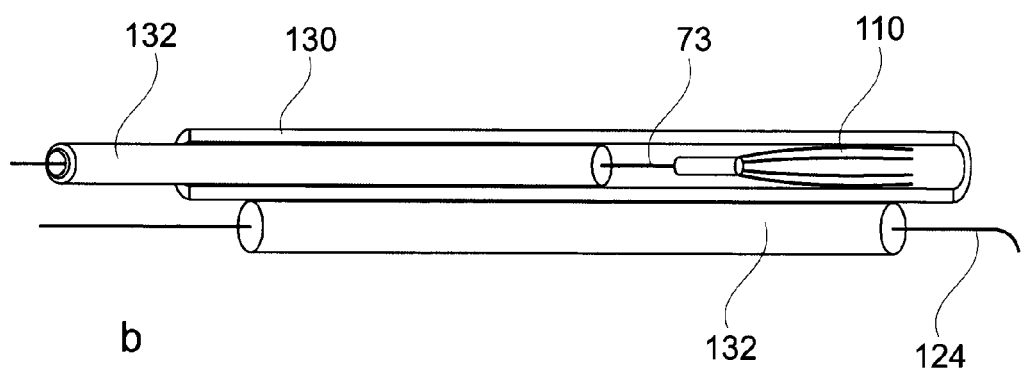
Fig. 24

DEVICE AND A METHOD FOR AUGMENTING HEART FUNCTION

RELATED APPLICATIONS

This application is a continuation of U.S. patent application Ser. No. 13/122,394 filed Oct. 18, 2011 entitled A Device And A Method For Augmenting Heart Function, which is a U.S. National Stage Application based on International Patent Application No. PCT/SE2011/050338 filed Mar. 25, 2011 entitled A Device And A Method For Augmenting Heart Function, which claims priority to U.S. Provisional Application Ser. No. 61/317,631 filed Mar. 25, 2010, and Swedish application Serial No. SE1050283-9 filed Mar. 25, 2010, both entitled Device And A Method For Augmenting Heart Function, all of which are hereby incorporated herein by reference.

FIELD OF THE INVENTION

The present invention relates to an intra-cardiac blood circulation enhancing apparatus, a system for intra-cardiac blood circulation enhancement and a method for enhancing left ventricular pump function of a patient. The present invention is in particular applicable to enhance the pump function of the left ventricle, including a permanent measure for treating a heart failure disease where the heart function is deficient.

BACKGROUND OF THE INVENTION

Where the heart function is chronically insufficient, there may be a need to permanently aid the heart function. Heart failure (HF), more often called Congestive Heart Failure (CHF), is in general a condition where the heart is unable to support the body tissue with its metabolic demands and to sustain adequate blood pressure and cardiac output. The term Congestive relates to a congestion of blood and fluids in front of the pumping ventricles as a result of insufficient forward pumping, most often caused by disease of the left ventricle muscle. A peculiarity of heart cells is that they do not regenerate after damage or cell death, thus conditions have a tendency to worsen rather than heal after heart cell damage. There are many reasons for heart cell death, the most common cause is ischemic heart disease, a condition where the arteries feeding the heart muscle get clogged, causing myocardial infarctions (MI). Viruses may damage the muscle cells, and some diseases, for instance cardiomyopathy have unknown reasons. End stage of long standing high blood pressure may also cause end stage heart failure. Heart strengthening drugs like digoxin or treatment with diuretics help for a while, but are all only treating symptoms. CHF is a progressive untreatable, disabling and finally a deadly condition. According to the American Heart Association homepage, there are in the US at present more than 5 Million patients living with CHF and 550 000 are added every year. 40000 patients in the US are in such a bad state that only a heart transplant will keep them alive. However, due to the limited number of suitable organs only 2500 transplants are done yearly in the US. One may extrapolate the numbers for the rest of the industrialized world.

Total artificial heart, where the whole native heart is excised and replaced with a mechanical device was introduced in the 1960's by DeBakey, in the 1980's by among others Jarvik and recently by Copeland (CardioWest, Total Artificial Heart). However, these devices are still based on complex designs and are very invasive to install in the patient. Failure in operation of the device is fatal.

There are other techniques supporting only the failing left ventricle, known as left ventricle assist devices (LVAD). The most popular LVADS are the Novacor and the HeartMate devices. Common for this devices is the demand for major open heart surgery utilizing extracorporeal circulation by means of a Heart- and Lung-machine while stopping (or excising) the heart. They are bulky devices, a Novacor weights 1.800 grams, a HeartMate 1.200 grams. There are smaller axial flow pumps available nowadays, the HeartMate II, the Jarvik 2000 and the MicroMed DeBakey VAD. However, major open heart surgery is still necessary to install and connect these devices to the left ventricle cavity and the aorta by means of large vascular grafts. The mentioned devices have almost exclusively been used as a bridge to a heart transplant due to high frequency of complications, some of which are caused by the large amount of foreign material, high mortality and limited durability. Their use has also been limited because of high prices of up to 150 000 $ only for the device.

In U.S. Pat. No. 5,957,977 an activation device for the natural heart is disclosed. The activation device has a stint for placement within the interior volume of a natural heart adjacent cardiac tissue thereof. The device also includes a yoke for placement around a portion of the exterior surface of the natural heart in general alignment with the stint and connected to the stint by at least one cord (surgical thread). By means of multiple parts that are assembled during surgery, a cage is created where half of the cage is inside the heart and the other half outside. Within the cage a heart chamber, e.g. the left ventricle is completely locked in. By means of hydraulic power underneath the external part of the cage, compression on the chamber is achieved from the outside. The inner half avoids that inner heart structures may give away while compressing from the outside. However, the device is very invasive, as it requires a connection between the interior of the heart and the exterior of the heart. Moreover, extensive open heart thoracic surgery is required to position the device in the patient, none of which involves surgery of the mitral valve. Furthermore, the device is not designed for action synchronic with the natural heart cycle.

None of the devices for permanent implant previously described are feasible for minimal invasive catheter based insertion. On the contrary, they all involve major open heart surgery. There is a need and demand for simpler devices. It is one scope of the here presented invention to omit major cardiac surgery and to allow positioning of an implant with catheter technique or by minimal access surgery.

Moreover, health care is permanently searching for improved devices and methods.

Hence, there is a particular need of an improved system and/or method for permanently enhancing or assisting left ventricular pump function of a heart of a patient. The system is advantageously not interfering with the cardiac cycle of the heart. Major open heart surgery is desired to be avoided. Even more advantageous would be if at the same time leaking heart valves could be repaired. It is also desired to avoid implantation of large surfaces of foreign material in the heart. Advantageously, the native valves, like the native mitral valve are preserved, when enhancing cardiac pump function with such devices.

Hence, an improved system and/or method for permanently enhancing or assisting left ventricular pump function of a heart of a patient would be advantageous and in particular allowing for increased flexibility, cost-effectiveness, long-term function, and/or patient friendliness would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device, a system, and a method according to the appended patent claims.

The here presented innovation is based on improved insight how the left ventricle functions.

Modern imaging of the beating heart has contributed largely to the understanding of left ventricle pump action. The pumping force of the left ventricle has before been understood to be totally a result of the heart muscle contracting and squeezing (systole) around the amount of blood enclosed inside the left ventricle after closure of the mitral valve, increasing the pressure and thereby forcing the blood towards the aortic valve, forcing this to open and ejecting the blood into the ascending aorta. When the squeezing is completed, an intermission occurs (diastole), during which a new portion of blood enters the left ventricle cavity from the left atrium.

Ultrasound imaging and Magnetic Resonance Imaging (MRI) has revealed that this previously taught mode of function is not completely true. Instead, one may describe two types of pump action, a long axis and a short axis action. MRI can show that there is a movement of the atrioventricular mitral valve (MV) plane downwards along the left ventricle long axis that extends from the atrium towards the ventricle's lower end, the apex. The left ventricle muscle cells are pulling the whole mitral valve plane, including the mitral valve annulus and part of the left atrial wall (that is stretching) towards the heart apex. By pulling the closed mitral valve towards the heart apex, the mitral valve becomes a piston in a blood displacement pump.

The downwards movement of the mitral valve is in a healthy human up to approximately 2 centimetres. The downwards movement accelerates the blood column away from the left atrium and towards the aortic valve in a continuous movement. By means of MRI technology one is able to virtually mark separate pixels inside the blood column and follow their movement. It is possible to show that the blood column flows more or less continuously from the left atrium to the ascending aorta without ever stopping. The blood column is accelerated by the mitral valve piston moving up and down along the cardiac long axis, opening every time it takes a new scoop of blood in an upward movement to the atrium, and closing just before moving back toward the apex. One may estimate the contribution of the long axis pump action of the heart to 30-50% of the total heart pump function.

In congestive heart failure the downwards movement of the mitral valve is impaired. It is the scope of the here presented innovation to augment the long axis function of the heart by means of improving the downwards and/or upwards movement of the mitral valve. To our knowledge, nobody has before attempted to enhance the up- and downwards movement of the mitral valve annulus by means of implanting an augmenting device.

The embodiments of the invention provide improved left ventricular pump action by means of external power in order to be able to move the native MV along the long axis of the left ventricle (LV) towards the heart apex, in synchrony with the cardiac cycle. A synchronized reciprocating movement of the MV valve plane is provided by various embodiments.

Major open heart surgery is avoided. Even when surgery would be done to implant some embodiments of the here presented device, it is limited to access the mitral valve annulus and the left ventricle, also providing an opportunity to repair a leaking mitral valve. The here described devices, systems and methods do not involve implantation of large surfaces of foreign material and the native mitral valve is in particular preserved in some embodiments.

In some embodiments, modern catheter based technology is integrated in the here described device, system and methods, allowing deployment of the whole system or parts of it by means of catheter technique.

According to one aspect of the invention, a medical device is provided for enhancing intra-cardiac blood circulation of a heart of a patient by assisting left ventricular pump action thereof. The device includes a displacement unit that controllably moves a mitral valve in a mitral valve plane substantially along a long axis of a left ventricle of the heart. The displacement unit is further configured to be arranged in the patient such that the mitral valve is moved in a reciprocating movement during systole towards an apex of the heart and during diastole away from the apex for assisting the pump action of the heart.

The displacement unit is in use moving the closed mitral valve during systole towards the heart apex and/or moving the opening or opened mitral valve during diastole away from the heart apex. The mitral valve thus becomes a supported piston in a blood displacement pump. The downwards movement accelerates the blood column away from the left atrium and towards the aortic valve in a continuous movement. The range of movement of the thus supported mitral valve along the long axis is up to approximately 2 centimetres in an adult patient. The range of movement is correspondingly less in pediatric patients and especially in patients with heart failure. The blood column acceleration by the mitral valve piston is assisted by the displacement unit, helping the mitral valve plane to move up and down along the cardiac long axis in a desired manner. The valve opens every time it takes a new scoop of blood in an assisted upward movement to the atrium, and closes just before assisted moving back toward the apex in the next systole. The assist movement provided by the displacement unit is made synchronously with the cardiac cycle to optimize the cardiac assist function provided.

In embodiments the displacement unit has a mechanical unit devised to apply a supporting force to the mitral valve during systole towards the apex, thus augmenting the (still existing) natural pumping force of the heart while ejecting blood into the aorta. In other embodiments the displacement unit includes a mechanical unit devised to apply a supporting force to the mitral valve away from the apex during diastole, augmenting the natural filling of the left ventricle of a heart, and thus augmenting the (still existing) natural pumping function of the heart by an improved filling degree. In preferred embodiments the invention is supporting the systolic as well as the diastolic function of a heart in synchrony with the heart cycle. The total force supplied to the mitral valve plane is the combined remaining natural force of the heart and the supporting force provided by the displacement unit.

This enhancement is done in a gentle way by supporting the natural function of the heart. Congestive Heart Failure (CHF) is effectively treated or prevented. Long term treatment is enabled. Invasiveness is very limited. The amount of foreign material implanted in the heart is very limited. Open heart surgery may not be necessary for installing some embodiments of the cardiac assist device.

In some embodiments, the mechanical unit has a proximal end at which it is attached to a location of the mitral valve, such as the mitral valve annulus. A distal end is attached to an energy converter unit that transfers energy from a remote energy source into a linear force and/or a rotational force for providing the supporting force. The mechanical unit is for instance a pulling and/or pushing unit. The pulling and/or pushing unit is attached to a location in the heart related to the mitral valve, such as the mitral valve annulus. The pulling and/or pushing unit is thereby in operation augmenting the natural force of the heart and extends the downwards and upwards movements of the mitral valve relative the apex. The movement of the MV plane along the long axis is thus supported, augmenting the natural force of the heart. Alternatively, or in addition, the mechanical unit may be based on other mechanical movement, such as a rotational, threaded, and/or pivotal based arrangement to provide the supporting force for the cardiac assist.

In some embodiments the mechanical unit is attached to the mitral valve annulus by means of a fixation unit. The fixation unit is for instance attached in a loop shaped manner, such as circular, along at least a portion of the mitral valve annulus, like an annuloplasty implant. The fixation unit may have the native form of the annulus circumference where the leaflets are attached. The annuloplasty implant may be provided in an annular (ring) shape, D-formed shape, open ring C-formed shape, etc. Regurgitation may thus be permanently treated conveniently by means of repair of a mitral valve. Being part of the displacement unit, heart pumping function is improved in a synergistic manner. The closing of the mitral valve leaflets during systole is improved by the annuloplasty, which in turn further improves the efficiency of the supported pump function provided by the supported displacement of the MV relative the apex.

Movable units of embodiments, like joints, etc. may be suitably encapsulated to not be in contact with blood or cardiac tissue to avoid any operational complications.

In some embodiments, the displacement unit has a plurality of magnetic tissue anchors that are controllably and selectively magnetic relative each other. A first anchor for instance located at the mitral valve, and a second anchor is located remote from the first anchor inside or outside the heart. This allows for a very compact arrangement without moving parts from a remote energy source. A controlled movement is for instance achieved by having at least one of the anchors being an electromagnet that controllably changes polarity synchronized with the heart cycle. One of the magnetic anchors may be a monolithic unit, which is a combined magnetic anchor and an annuloplasty implant (shape see above). Magnetic functionality may be added by a coil unit. The coil unit may be integrated with the annuloplasty implant. Alternatively, the coil unit may be provided as a flange unit allowing for affixing the annuloplasty implant or anchor unit to the annulus tissue in a convenient manner.

The second magnet anchor may also be located in the atrial or ventricular septum, wherein the second anchor unit may be occluding an (natural) opening in the septum. The occluder anchor may have two flange units for apposition to the septum on the left respectively the right heart side with an interconnecting portion of reduced diameter arranged in the opening. The occluder anchor is made of a magnetic material or provided with electromagnetic properties. Septal defects may thus be treated, and heart function is improved conveniently in a synergistic manner. Septal occlusion and supported MV movement, eventually with reduced regurgitation, provide for optimized heart function.

The second magnet anchor may be located in the left atrial appendage (LAA), wherein the second anchor unit is an LAA occluder. The LAA occluder may have one or more retention flanges for safe anchoring in the LAA. The LAA occluder anchor may have two flanges. The occluder anchor LAA is made of a magnetic material or provided with electromagnetic properties. LAA related diseases, such as embolic events, may thus be treated conveniently at the same time as supported heart function is provided. Heart diseases are thus treated in a synergistic manner.

In embodiments the displacement unit is driven by energy from an energy source providing the energy for the movement of the mitral valve in the mitral valve plane along the long axis. The energy is e.g. movement energy that is mechanically transferred from a remote energy source to the displacement unit. Alternatively, or in addition, the energy is electrical energy that is transferred from the remote energy source via a cable to an actuator of the displacement unit.

In the displacement unit the mitral valve may be a replacement artificial valve that is moved along the long axis of the left ventricle reciprocating towards the heart apex and away therefrom in synchrony with the cardiac cycle. Cardiac assist function may then be provided as in other embodiments by providing a movement of the MV plane of the replacement valve along the LV long axis. Alternatively, the replacement valve may be arranged to move up and down in a support frame to provide the cardiac assist reciprocating movement along the LV long axis.

In some embodiments an anchor unit of the displacement unit is provided in form of a foldable mitral valve annulus anchor unit affixable to the mitral valve annulus. The unit is thus retractable into a catheter and minimal invasive procedures are facilitated.

The displacement unit may be bistable between a stable diastolic up position and a stable systolic down position of the MV plane, wherein the displacement unit has an equilibrium state in the up and down position respectively, and wherein the displacement unit moves between the two stable positions when energy from an external energy source is controllably provided to the displacement unit in synchrony with the cardiac cycle. These embodiments may be more energy efficient than others.

In embodiments the cardiac assist device has a control unit and a sensor for measuring physiological parameters related to the cardiac cycle activity providing a sensor signal. The sensor signal is provided to the control unit which controls the displacement unit to provide the movement by energy from an energy source and based on the sensor signal. The cardiac assist device operation is thus controlled in synchronicity with the heart action. The sensor may be ECG electrodes or in addition or alternatively be based on detecting one or more other physiological parameters related to the cardiac activity, such as a blood pressure wave, acoustic heart sounds, and/or blood flow patterns.

The energy source may be located in tissue under the skin, adjacent to a vessel, such as a large vein. This allows for convenient access to the displacement unit.

In another aspect of the invention, a kit is provided that includes medical device of the above aspect of the invention and a delivery system for the device. The delivery device may include an introducer catheter with a valve, a guiding catheter, a guide wire and at least one delivery catheter.

The device and kit may be used in medical procedures.

One medical procedure concerns delivering such a medical device to enhance intra-cardiac blood circulation of a heart of a patient by assisting left ventricular pump action. The method includes providing a medical system including the medical device and an energy source, and surgically and/or minimally invasively delivering the medical system in the patient.

The method may include providing a delivery system, such as of the aforementioned kit, for minimally invasively delivering the medical device in the patient, and minimally invasively delivering the displacement unit of the medical system in the patient by means of the delivery system, delivering the energy source, and connecting the energy source and the displacement unit.

The delivery system may include an introducer catheter with a valve, a guiding catheter and a guide wire. The method then may include introducing the introducer catheter at a puncture site into the vascular system of the patient, inserting the guide wire into the vascular system via the introducer catheter, navigating through the vasculature and the heart to a desired site, inserting the guiding catheter over the guide wire, withdrawing the guide wire, through the guide catheter delivering a first anchor unit at a mitral valve and delivering a second anchor unit at a distance from the mitral valve.

The delivery system may include an introducer catheter with a valve, a delivery catheter and a pushing unit, a guide wire and a guiding catheter. The method then may include introducing the introducer catheter at a puncture site into the vascular system of the patient, inserting the guide wire into the vascular system via the introducer catheter, navigating through the vasculature and the heart to a delivery site, inserting the guide catheter over the guide wire, providing an anchor unit at a distal end of the pushing unit, introducing the distal end in front of the pushing unit into the delivery catheter. The delivery catheter may have a smaller outer diameter than an inner diameter of the guiding catheter, and the method includes longitudinally moving the delivery catheter in the guide catheter. Alternatively, the method includes retracting the guide catheter, and longitudinally moving the delivery catheter over the guide wire previously placed at the delivery site by means of the guide catheter. Further, the method includes activating the anchor unit by means of pushing the pushing unit forward while the tip of the delivery catheter has contact with the surface of delivery site, such as the left ventricle wall, and allowing anchor elements of the anchor unit, such as hooks or blades to dig into the tissue at the delivery site.

The pushing unit may be a catheter itself, small enough to fit coaxially inside the outer delivery catheter. The pushing unit may have a central lumen allowing the pulling and pushing unit to pass there through all the way from outside of a patient and through his or hers vascular system. The anchor element may have hooks, and be retracted into the delivery catheter so that the hooks of the anchor are having the tips facing forward towards the catheter opening. Alternatively, or in addition, a separate lumen may be attached, or integrated with, at least to part of the delivery catheter. The guide wire lumen may also be inside the delivery catheter.

The method may further include threading an extension unit through the delivery system and releasing a mitral valve annulus anchor by retracting the catheter of the delivery system from over the mitral valve annulus anchor, and attaching the mitral valve annulus anchor to the mitral valve annulus.

The method may include providing access to the vascular system by puncturing a large vein, placing an introducer catheter with a valve in the vein, through the introducer catheter advancing a guide wire, and over the guide wire advancing a guide catheter to the right atrium, obtaining access to the left atrium by penetrating through an open foramen ovale or through the inter-atrial wall and thereafter advancing the guiding catheter into the left atrium, and advancing the guide catheter and the guide wire into the left ventricle through the mitral valve to the delivery site at the left ventricular wall, advancing a delivery system for an anchor inside the guide catheter or over a guide wire until its catheter opening has contact with the inner surface of the left ventricular wall, advancing the pushing catheter and pushing the anchor out of the catheter opening to dig into the muscular tissue and pull the anchor inside the musculature, and thereby creating a secure anchoring of a pulling and pushing unit, and retracting the delivery catheter and pushing unit.

The method may include advancing a delivery system for a mitral valve annulus anchor over the pulling and pushing unit until the anchor and its arms are adjacent to the mitral valve annulus, and when in position, retracting the catheter until outside of the patient, allowing arms and their attachments hooks to attach to the mitral valve annulus and dig into the tissue.

The method may further include adjusting the pushing and pulling unit and the catheter in length and attaching to the remote energy source.

The method may include positioning the remote energy source in fatty tissue under the skin, adjacent to a vessel, such as a large vein as the subclavian vein, and optionally attaching the energy source to a bony structure, such as the clavicle.

Some methods may include providing surgical access to the mitral valve, the mitral valve annulus and the left ventricle including surgically opening the chest of a human being and establishing extra corporeal circulation (ECC) or manipulating the heart manually from the outside, while still pumping.

The method may include attaching a first anchor unit in the musculature in the area of the inside left ventricular apex, outside on the left ventricular apex, or in adjacent tissue, attaching a second anchor unit to the mitral valve annulus, and connecting the two anchors to each other by means of a connecting unit that may shorten and increase the length between the anchors, attaching the connecting unit to a remote energy source. Alternatively, the method may include replacing the mitral valve by an artificial valve unit serving as both the mitral valve and the mitral annulus anchor.

In another aspect, a method is provided for permanently enhancing left ventricular pump function of a heart of a patient, the method comprising controlled assisted mitral valve movement synchronized with a cardiac cycle of the heart.

The method may include providing a medical device adapted to enhance intra-cardiac blood circulation of a heart of a patient by assisting left ventricular pump action, the device having a displacement unit, and controllably moving a mitral valve in a mitral valve plane substantially along a long axis of a left ventricle of the heart by the displacement unit, wherein the controllably moving includes moving a mitral valve in the heart in a reciprocating movement during systole towards an apex of the heart and during diastole away from the apex for assisting the pump action of the heart, and activating the medical device.

The method may include detecting the natural action of the heart, such as by measuring an electrocardiogram, heart sounds, a blood pressure wave or blood flow of the heart, and providing energy for displacement of the mitral valve in synchrony with the natural heart cycle, thereby enhancing the natural up and down movement of a mitral valve during a heart cycle.

The method may include providing a mitral valve replacement valve for the movement. The replacement valve may be mounted in a housing, and moving the heart valve up and down in the housing relative to a mitral valve annulus attachment.

Moreover, a system is provided for permanently enhancing left ventricular pump function of a heart of a patient, the system includes a displacement unit for controlled assisted mitral valve movement synchronized with a cardiac cycle of the heart.

According to another aspect, a computer-readable medium having embodied thereon a computer program is provided for processing by a computer for permanently enhancing left ventricular pump function of a heart of a patient, the computer program comprising a code segment for synchronizing assisted mitral valve movement in relation to the heart apex with a cardiac cycle of the heart.

According to an aspect of the invention, there is provided a kit for permanently enhancing the left ventricular function of a heart. The kit includes a left ventricular enhancement or augmentation system placed in the left ventricle, the left atrium and the mitral valve, and in adjacent tissue able to move the mitral valve plane, its annulus and leaflets along the direction of the long axis of a left ventricle in synchrony with the heart cycle, an energy source and a delivery system for carrying the augmentation system to desired positions in the heart.

The kit may provide a convenient package to a surgeon who is about to introduce an enhancement system into a patient. Thus the kit provides both implants that may be used for permanently treating the patient and a delivery system which may be used for inserting the implants. The enhancing means may be pre-mounted in the delivery system for storage, while the energy source may be packaged separately for connection during surgery. The kit may further have a guide wire for guiding insertion of the delivery system to the desired positions through the vascular system of a patient. The delivery system may also have a guiding catheter which is arranged to be pushed over the guide wire to the desired position. Also an introducing catheter for establishing access to the vascular system by a percutaneous access may be part of the kit. A valve that is prohibiting blood backflow but still allows a guide wire or a guiding catheter to pass through is preferably included in the introducing catheter.

According to a further aspect of the invention there is provided a method for permanently treating failure of a left ventricle in a patient. The method includes inserting a left ventricular enhancement system into the left ventricle, the left atrium and adjacent tissue and arranging an enhancement unit of the enhancement system in desired positions such that the enhancement unit may be connected to an energy source unit. The method includes transfer of external energy to the enhancement unit in the left ventricle, the left atrium and adjacent tissue in order to move the mitral valve up and down along an axis from the left atrium towards the left ventricular apex, i.e. the long axis, synchronized with the natural heart cycle.

In embodiments, the method includes also insertion of an energy source under the skin.

The method allows for connection of electrical cables or device extensions for transferring power to the energy source in such a way that the energy source may be located under the skin but outside a vein.

Further, the method may involve transfer of electrical energy through the skin either by cable or electro-magnetically in order to store electrical energy in a battery under the skin.

In addition hereto the method may include the use of computer chips and algorithms in order to detect the spontaneous cardiac cycle and guide the enhancing system in accordance to the heart cycle by means of detecting an electrocardiogram.

A preferable method of placing an energy source would be to do this surgically through a small incision in the skin and make a small pocket in the subcutaneous tissue under the skin. Part of the method would be to use the same pocket to gain access to a vein by means of puncturing the introducer catheter into the vein through the pocket.

Still another part of the method would be to get access to inside of the left heart by means of puncturing an artery in order to place anchors.

Further it is part of some embodiments of the method to attach an anchor to the inside or walls of the ventricles, the mitral valve annulus or the atria by means of hooks. An alternative method is to attach an anchor to the wall of the ventricles by inserting it from the outside of the heart through a small surgical incision.

Further, parts of the system may be implanted by surgical means while the heart is stopped and its function temporarily is provided by a heart- and lung-machine.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings.

FIGS. 5-9 are schematic illustrations depicting how various embodiments augment the mitral valve movement along the left ventricular long axis.

FIGS. 10 *a* and *b* are schematic illustrations that describe different embodiments utilizing pulling and pushing forces in order to augment the mitral valve movement.

FIGS. 11 *a-c* are schematic illustrations that describe different embodiments utilizing a linear actuator in order to augment the mitral valve movement.

FIGS. 22-27 are schematic illustrations that show a delivery system for complete catheter based insertion of the heart function augmentation system.

DESCRIPTION OF EMBODIMENTS

Figure 2:
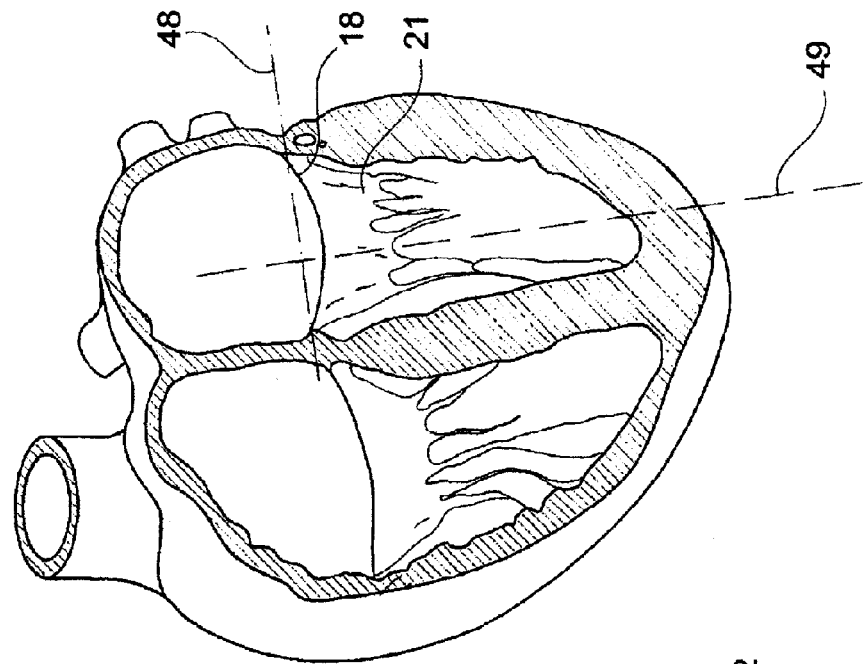
FIG. 2 is a schematic illustration showing the level of the mitral valve plane in relation to the left ventricular long axis.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The embodiments of the invention provide improved left ventricular pump action by means of external power in order to be able to move the native MV along the long axis of the left ventricle (LV) towards and/or away from the heart apex, in synchrony with the cardiac cycle. The here described permanent implant will not take over or replace the remaining natural left ventricular pump function, it rather augments the pump function. A synchronized supported up and/or down movement is provided of the mitral valve that works as a piston, when it is closed.

Figure 1:
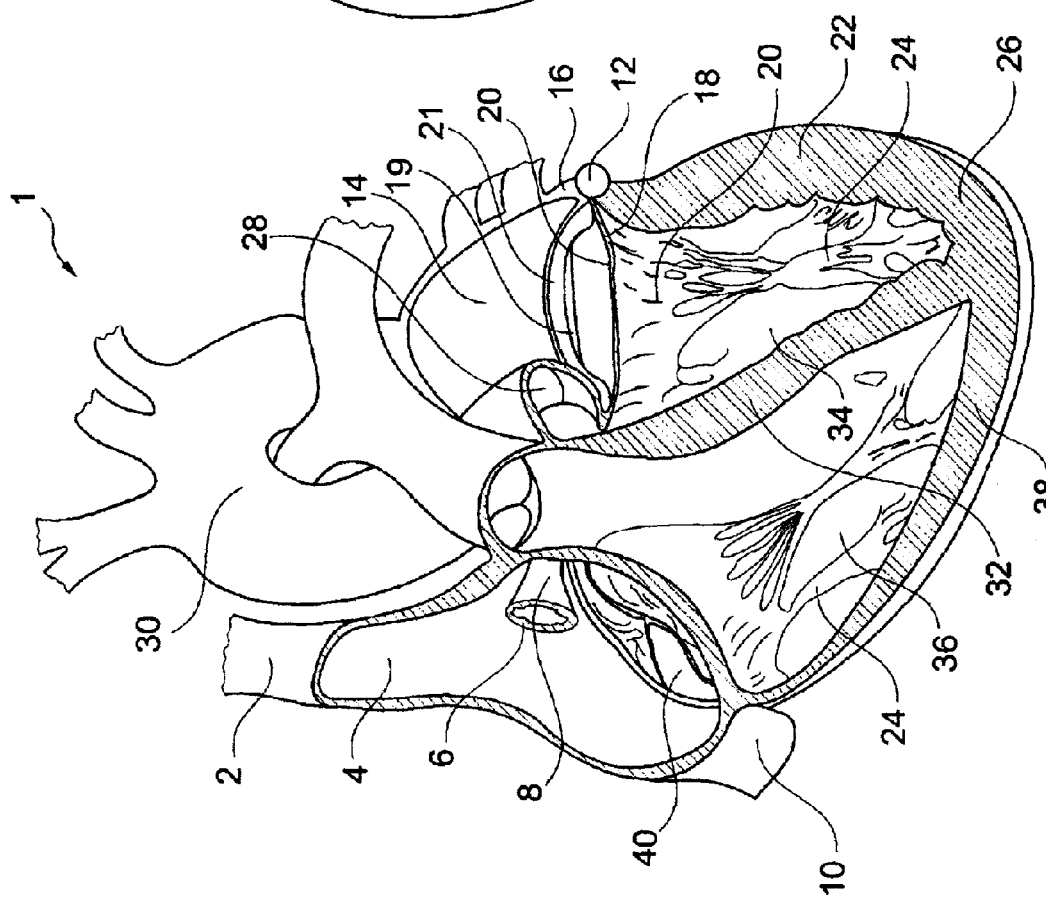
FIG. 1 is a partly cross-sectional schematic illustration of a human heart depicting structures that are involved.

FIG. 1 depicts the anatomical structures of the heart 1, of which at least some are involved in embodiments of the invention. 2 is the Superior Vena Cava (SVC), 4 is the right atrium (RA), 6 is the Coronary Sinus (CS) ostium, 8 is the CS first part. 10 is the Inferior Vena Cava (IVC), 12 is the Great Cardiac Vein (GCV) at the level of the MV annulus 18. 14 is the Left Atrium cavity (LA), 16 is the LA wall, 18 is the mitral valve annulus, 19 the whole mitral valve, 20 is the anterior leaflet and 21 is the posterior leaflet of the mitral valve. 22 is the LV muscular wall, 24 are the papillary muscles connected to the chordae, 26 is the apex of the left ventricle. 28 is the aortic valve, 30 the aorta ascendens, 32 the inter-ventricular muscular septum, 34 the left ventricular cavity and 36 the right ventricular cavity. 38 is the right ventricular muscular wall and 40 is the tricuspid valve.

FIG. 2 shows the mitral valve plane 48 in relation to the long axis 49 of the left ventricle. As can be seen, the LV long axis 49 is close to perpendicular to the MV valve plane 48.

Figure 3:
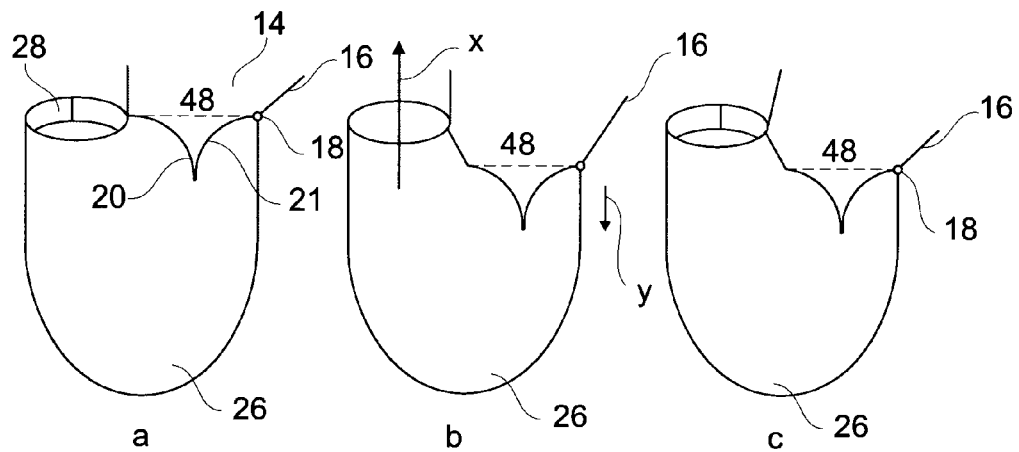
FIGS. 3 and 4 are schematic illustrations explaining the normal movement of the mitral valve during a normal cardiac cycle.
Figure 4:
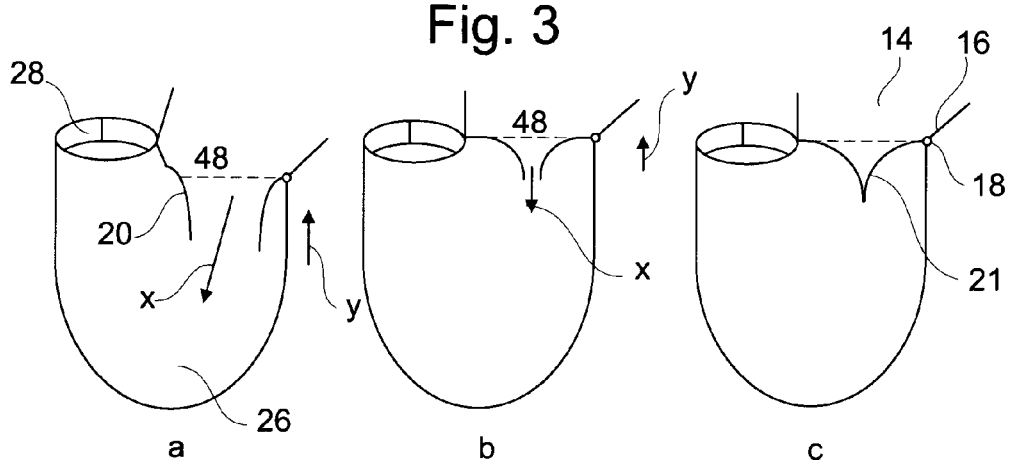

FIG. 3 is a schematic view of the natural, non-supported movements in systole of the mitral valve plane 48 in relation to the LV apex 26, the MV anterior 20 and posterior 21 leaflets, the MV annulus 18, the aortic valve 28, the LA wall 16 and the LA cavity 14 during a normal heart beat cycle. The large arrow (x) shows the direction of the blood flow and the small arrow (y) the direction of MV plane. In the cardiac cycle, the following moments are shown in FIG. 3: a) immediately before systole, b) during systole and c) at the end of systole. The piston movement (y) of the mitral valve plane 48 during systole, pushing the blood out of the aortic valve 28 can clearly be seen. In a diseased heart, this natural systolic movement may be deteriorated. FIG. 4 is a schematic view of the natural, non-supported movements in diastole of the mitral valve plane 48 in relation to the LV apex 26, the MV anterior 20, and posterior 21 leaflets, the MV annulus 18, the aortic valve 28, the LA wall 16 and the LA cavity 14 during a normal heart beat. The large arrow (x) shows the direction of the blood flow and the small arrow (y) the direction of the MV plane 48. In the cardiac cycle, the following moments are shown in FIG. 4: a) early diastole, b) late diastole and c) end of diastole. In a diseased heart, this natural diastolic return movement may be deteriorated. At the end of diastole the mitral valve is now closed and ready for the next movement downwards along the long axis of the left chamber in the following systole.

In a diseased heart, for instance, the range of movement of the MV plane may be reduced, e.g. due to heart muscle insufficiencies. Further, other motion parameters, such as the acceleration and/or maximum velocity component of the MV plane movement may be reduced.

Embodiments as described below assist the remaining natural movement in a diseased heart and thus may provide for an at least partial restoration of the aforementioned motion parameters, such as the range of movement and/or acceleration and/or maximum velocity component of the MV plane movement either during systole, diastole or both.

Figure 5:
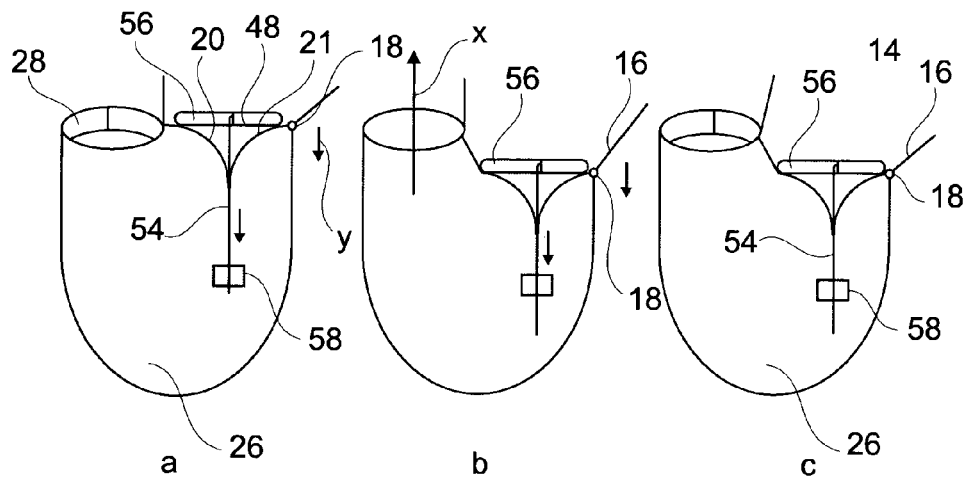
Figure 6:
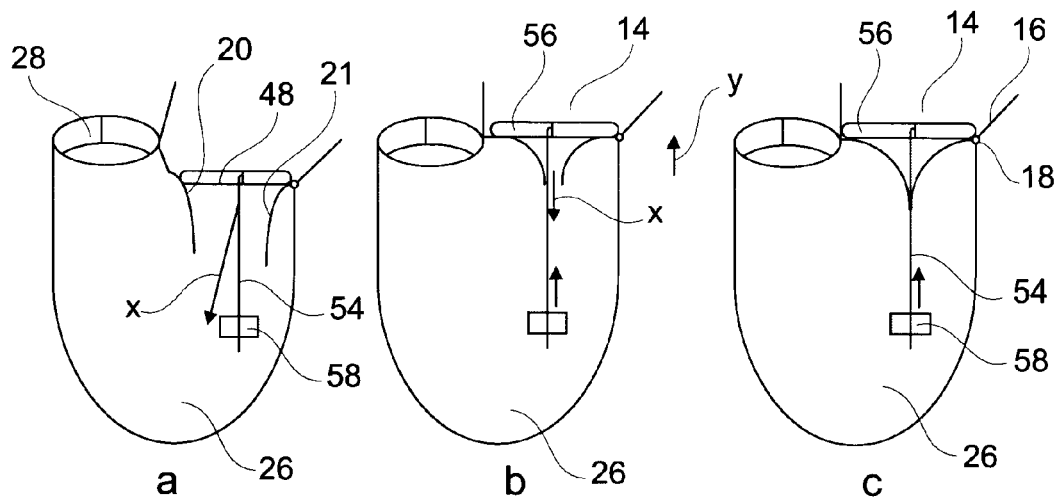

FIGS. 5 and 6 are schematic views of an embodiment of the invention when inserted in the heart 1. FIG. 5 depicts, as in FIG. 3, the movements in systole of the mitral valve plane 48 in relation to the LV apex 26, the MV anterior 20 and posterior 21 leaflets, the MV annulus 18, the aortic valve 28, the LA wall 16 and the LA cavity 14 during an augmented heart beat.

A pulling and pushing unit 54 applies a supporting force to the MV. The pulling and pushing unit 54 forces the MV downwards towards the LV apex during systole and away from the LV apex during diastole. The supporting force is generated by means of external power unit 84 and a power actuator 58 supplied to the pulling and pushing unit 54. The pulling and pushing unit 54 is thereby augmenting the natural force and extends the downwards movement of the mitral valve 19. The movement of the MV plane 48 along the long axis 49 is thus supported, augmenting the natural force of the heart. The support makes the cardiac pumping action more effective, i.e. cardiac output CO is enhanced. At the same time the cardiac muscle is relieved. The large arrow (x) shows the direction of the blood flow and the small arrow (y) the direction of MV plane.

The pulling and pushing unit 54 may in some embodiments either actively push, pull, or perform both active push and active pull action. The pulling and pushing unit 54 is then a pulling and/or pushing unit. This selection of pulling and/or pushing is done in dependence if assistance of the MV plane movement is to be provided during systole or diastole or both. In case only one of the pulling or pushing action is actively assisting the MV plane movement, the other pushing or pulling action is made passively (without assisting the natural movement) to return to the initial position. For instance the MV plane may only be actively moved towards the LV apex during systole (either by pulling or pushing), and the return during diastolic filling may passively be made (correspondingly by pushing or pulling) without assisting the natural movement.

Embodiments where only the systole or diastole, or portions thereof, are assisted, may provide for reduced energy consumption of the medical assist device, leading to advantageously enhanced battery life, etc.

The pulling and pushing unit 54 is at the proximal end attached to a location of the mitral valve, for instance the MV annulus. Attachment is made by means of a fixation unit 56. The fixation unit 56 is for instance attached circular along the mitral valve annulus 18, like a loop shaped annuloplasty ring. The other, distal end of the pushing and pulling unit 54 is attached to an energy converter unit 58 that transfers energy from the remote energy source 84 (not shown) into a linear force. Energy from the remote energy source 84 is in some embodiments provided as electrical energy. A small linear actuator or an electrical motor is suitable. In the cardiac cycle, the following moments are shown in FIG. 5: a) immediately before systole, b) during systole and c) end of systole.

FIG. 6 depicts, as in FIG. 4, the movements in diastole of the mitral valve plane 48 in relation to the LV apex 26, the MV anterior 20 and posterior 21 leaflets, the MV annulus 18, the aortic valve 28, the LA wall 16 and the LA cavity 14 during an augmented heart beat. The pulling and pushing unit 54 forces by means of external power 84 (not shown) the mitral valve ring along the long axis towards the left atrium, and is thereby augmenting the natural cardiac upward force, extending and supporting the upwards movement of the mitral valve 19 towards the LA. Thereby the device is enhancing the diastolic filling of the LV before the next heart beat. The large arrow (x) shows the direction of the blood flow and the small arrow (y) the direction of MV plane. In the cardiac cycle, the following moments are shown in FIG. 6: a) early diastole, b) late diastole and c) end of diastole, the mitral valve is now closed and ready for the next systolic downwards movement.

A prototype of the invention was built, using a linear accelerator and a computer. The computer allowed action in synchrony with an electrocardiogram. The prototype was tested in an animal experiment. The chest of a 60 kilogram pig was opened between the ribs. A rod from the linear accelerator was attached to the mitral valve annulus from the outside of the heart. The heart function was depressed by means of drugs. After activating the device an increase in arterial blood pressure and cardiac output was observed.

Figure 7:
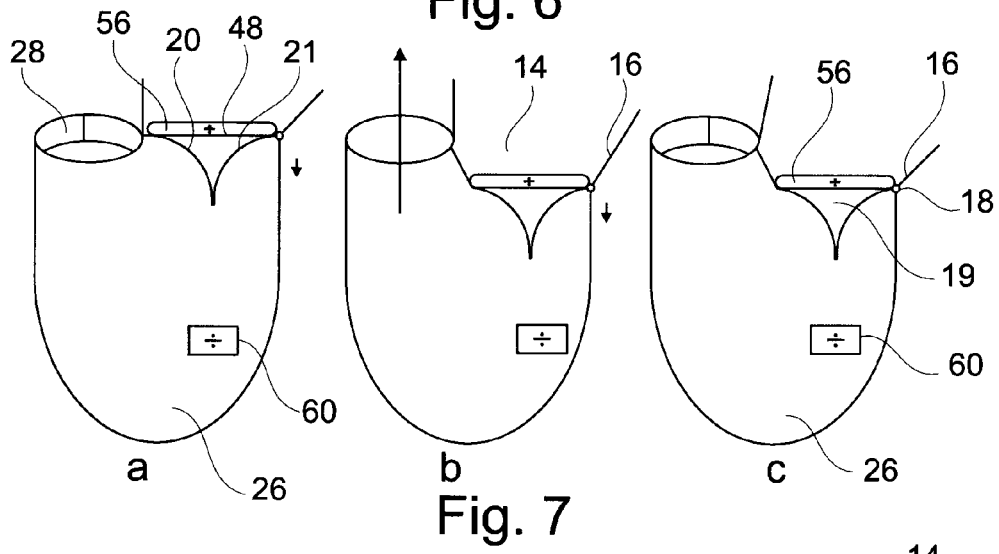
Figure 8:
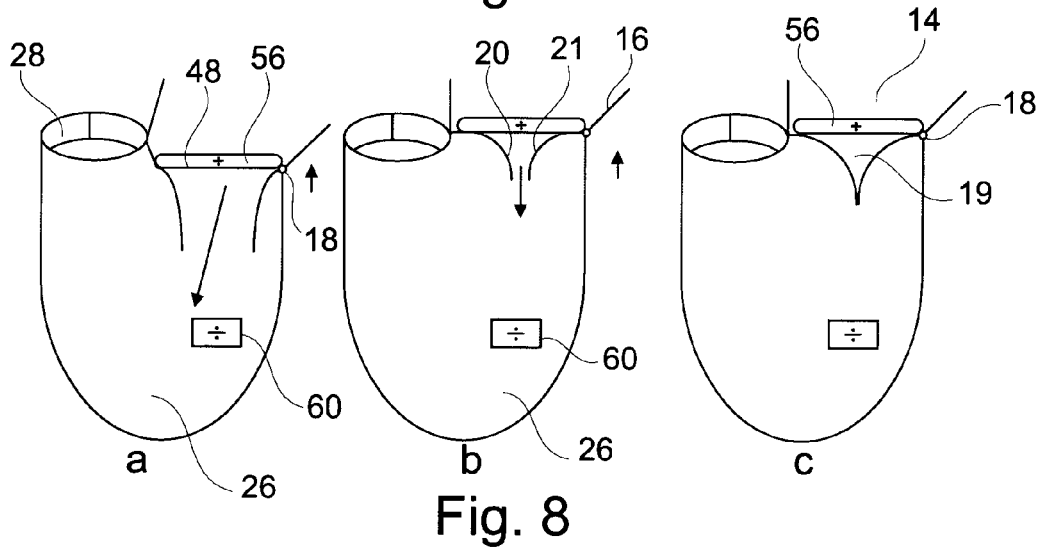

FIGS. 7 and 8 are schematic views of another embodiment when inserted in the heart 1. The device has two magnetic tissue anchors, namely a first, proximal magnetic anchor 56 and a second, distal magnetic anchor 60. The anchors 56, 60 are controllably and selectively magnetic relative each other, allowing for a controlled movement. The first anchor 56 is located at the MV, e.g. as a loop shaped ring affixed to the MV annulus 18. The second anchor unit 60, is located in the LV cavity, e.g. affixed in its wall 22. Alternatively, the second anchor 60 is attached to the LV outer wall. The two anchors are magnets, preferably electromagnets, but one or the other may also be a traditional permanent magnet. The electromagnetic magnets are arranged to change polarity, synchronized with the heart cycle in order to change between pulling towards each other and/or pushing away from each other. There are no physical connecting units between the anchor units, which allows for an optimal movement along the LV long axis, which may not entirely be perpendicular to the MV plane. When the anchoring units have different polarity they move the two anchors closer to each other and correspondingly, when the polarity is equal, they move the two anchors away from each other. FIG. 7 depicts, as in FIG. 3, the movements in systole of the mitral valve plane 48 in relation to the LV apex 26, the MV anterior 20 and posterior 21 leaflets, the MV annulus 18, the aortic valve 28, the LA wall 16 and the LA cavity 14 during an augmented heart beat. The first magnetic anchor 56 (positive charged) and the second magnetic anchor 60 (negative charged) attract each other and thus by means of magnetic power the two anchors are attracted closer to each other. This magnetic based supporting force is thereby augmenting the natural cardiac muscle force and the downwards movement of the mitral valve 19 is supported. The large arrow shows the direction of the blood flow and the small arrow the direction of MV plane, and the magnet 56. In the cardiac cycle, the following moments are shown in FIG. 7: a) is immediately before systole, b) during systole and c) end of systole.

FIG. 8 is a schematic view of the same embodiment as in FIG. 7 in diastole. FIG. 8 depicts, as in FIG. 4, the movements in diastole of the mitral valve plane 48 in relation to the LV apex 26, the MV anterior 20 and posterior 21 leaflets, the MV annulus 18, the aortic valve 28, the LA wall 16 and the LA cavity 14 during an augmented heart beat. The magnetic anchors 56 and 60 now have equal polarity (here both negative) and push each other away. The magnetic power thus forces the two anchors from each other, and is thereby augmenting the natural cardiac force and supports the upwards movement of the mitral valve 19, namely the MV plane 48 upwards along the long axis 49. The large arrow shows the direction of the blood flow and the small arrow the direction of the MV plane and the magnet 56. In the cardiac cycle, the following moments are shown in FIG. 8: a) early diastole, b) late diastole and c) end of diastole.

FIG. 9 shows alternative positioning of the second magnet anchor 60. The second anchor 60 can be electromagnetic or classic permanent magnetic. In embodiments where the second magnet 60 is permanent magnetic, the first magnetic anchor 56 is an electromagnetic with selectively activateable magnetic polarity. The second anchor 60 can be placed in different positions in the heart. However, positions outside the heart are also possible in certain embodiments. Location 61 indicates a position where the second anchor 60 is not attached to or in the heart. One such position is in the pericardium. Another position is in the pleura or under the skin. Possible alternative attachment sites include the pericardium, or the diaphragm. The spine or the thoracic cage (ribs and sternum) are also suitable sites for attachment of the second anchor 60. Positions 62, 64, 66, 68 indicate positions for the second magnet anchor 60 relative the heart. Position 62 is located in the left ventricle and position 64 is located in the right ventricle. Position 66 is located in the RA, preferably in the so called atrial septum between the RA and the LA. One good position is in the foramen ovale of the atrial septum where often an opening is present to the LA. In this embodiment, the second anchor unit may have the shape of a septal occluder and provide both septal leakage occlusion and allows for support of the cardiac function. Position 68 indicates a position in the LA, again a good attachment site would be the atrial septum, another good position in the LA would be the LA appendage (LAA, not shown). In this embodiment, the second anchor unit may have the shape of an LAA occluder and provides both LAA occlusion and allows for support of the cardiac function. These are only examples and a person skilled in the art may think of multiple variations that would work equally well for the purpose.

Alternatively, or in addition, more than two second anchor units may be provided accordingly. This may allow for smaller size of each second anchor unit compared with a single second anchor unit. Alternatively, or in addition, the first anchor unit may comprise a plurality of sub units, allowing for similarly reduced size and implanted mass of each sub unit compared to a single, integral or monolithic, first anchor unit.

Electrical power for the mini motors, electromagnets or linear actuators is in embodiments provided from the remote energy source 84 by means of insulated cables 76.

Alternatively, or additionally, in other embodiments, such as shown in FIGS. 10*a* and 10*b* the energy is transferred mechanically from the remote energy source 84 through an extended connecting unit 73. The connecting unit 73 may be arranged as a Bowden cable type, having a movable inner wire surrounded by a sheath 78. The connecting unit 73 extends all the way from a tissue anchor 72, through the mitral valve attachment unit 56. The tissue anchor 72 shown here is deployed in the LV muscle wall 22 near the apex 26. The anchor has hooks 75 that dig into the tissue for a strong attachment. One attractive option is to drop the anchor prior to the mitral annulus attachment in order to let it grow into the tissue and create a strong scar tissue before connection to the energy source and starting the action of the device. A good interval would be to allow ingrowth during 6-8 weeks prior to starting cardiac assist operation of the device. The guiding sheath 78 is at its distal end fixated in the mitral annulus anchor 56 and at its proximal end at the energy source 84. In this way the following cardiac assist operation is provided. When proximally pulling the connecting unit 73 (relative to the guiding sheath 78), e.g. from an actuator at or inside the energy source, the distance between the tissue anchor 72 and the MV fixation unit 56 will shorten. When pushing the connecting unit 73 (relative to the guiding sheath 78) proximately at the remote energy source, the distance between the tissue anchor 72 and the MV fixation unit 56 increases. In this manner, cardiac assist is provided by supporting the MV plane 48 movement along the long axis 49. FIG. 10a depicts the situation when the extended connecting unit 73 is pushed against the anchor 72. The mitral valve is then pushed upwards in its diastolic position. FIG. 10b accordingly shows the opposite situation in systole when the extended connected unit 73 is pulled relatively to the sheath 78. The distal end of the sheath 78 is affixed to the MV fixation unit 56. Thus, the mitral valve is being pushed down in systole, towards the LV apex 26. The mitral valve is thus brought closer to the apex 26, assisting the systolic natural movement of the heart.

Turning to FIG. 11a, another embodiment is shown where the external force is executed by means of an actuator. The electrical power is supplied by the remote energy source 84 (not shown) by means of a cable 76. Here the cable connects to the energy source through the vascular system. The actuator may advantageously be constructed as a mini linear actuator now available on the market. The actuator may alternatively, or in addition, have a mini motor integrated. MEMS (micro-electro-mechanical-systems) technology may be utilized for constructing such a motor. Thus FIG. 11a depicts the situation when the connecting unit 54 is pushed against the mitral valve annulus attachment 56. The mitral valve will then be pushed upwards in its diastolic position. In FIG. 11b accordingly, the opposite situation is shown in systole, when the connecting unit 54 is pulled towards the actuator 58. The mitral valve is thus being pulled down in systole and the mitral valve is brought closer to the apex 26. Here, an electrical cable 76 is connected to the remote energy source 84 outside the vascular system.

In FIG. 11c it is illustrated that the axial actuator 58 not necessarily needs to be arranged inside the LV cavity. As depicted here, it may also be attached to the heart wall close to the apex 26.

FIGS. 12 a-b show examples of configurations described in FIGS. 7, 8 and 9, where electromagnets are used as tissue anchors 56. Further combinations of electromagnets and classical permanent magnets will not be described in relation to separate figures as such combinations will be apparent for the skilled person when reading the examples given herein.

In FIG. 12 a, one second anchor unit 60, e.g. a permanent magnet, is located in the left ventricular wall close to the apex 26. The counter magnet unit, in form of a first anchor unit 56, serves as an attachment to the mitral valve annulus 18. The first anchor unit 56 is as well an electromagnet that may change polarity according to the heart cycle. A known loop shaped annuloplasty implant may be used with added magnetic functionality for the first anchor unit 56. Such annuloplasty implants may be provided in an annular shape, D-formed shape, open ring C-formed shape, etc. Magnetic functionality may be added by a coil unit. The coil unit may be integrated with the ring, or made easy to attach. Alternatively, the coil unit may be provided as a flange unit allowing for affixing the implant to the annulus tissue in a convenient manner.

Figure 12A:
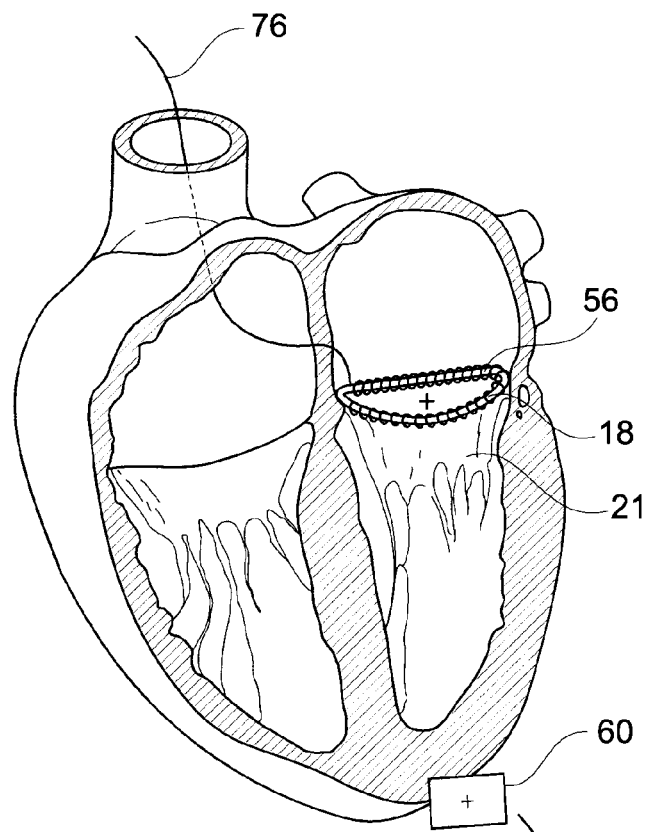
FIGS. 12 *a-b* are schematic illustrations that depict an embodiment using magnetic force in order to augment the mitral valve movement.
Figure 12B:
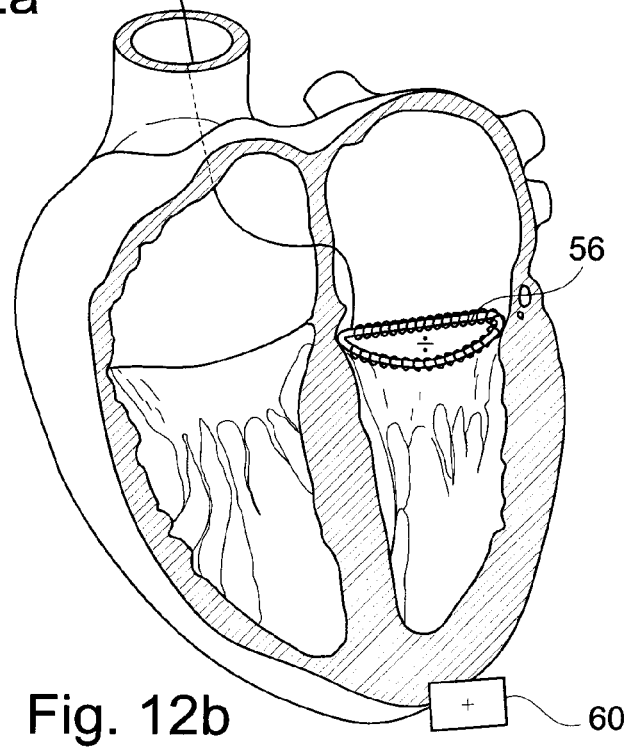

FIG. 12a depicts the situation in diastole, where both magnetic units have the same polarity, here the poles are illustrated positive. Thus the mitral valve is pushed away from the LV apex, towards the LA. The mitral valve plane is re-positioned upwardly along the LV long axis. Contrary to this, FIG. 12b shows the situation in systole. The polarity of the magnet unit in the mitral valve has changed polarity, here to negative, attracting the positive charged magnet unit in the apex and pulling the mitral valve against the apex.

Figure 13A:
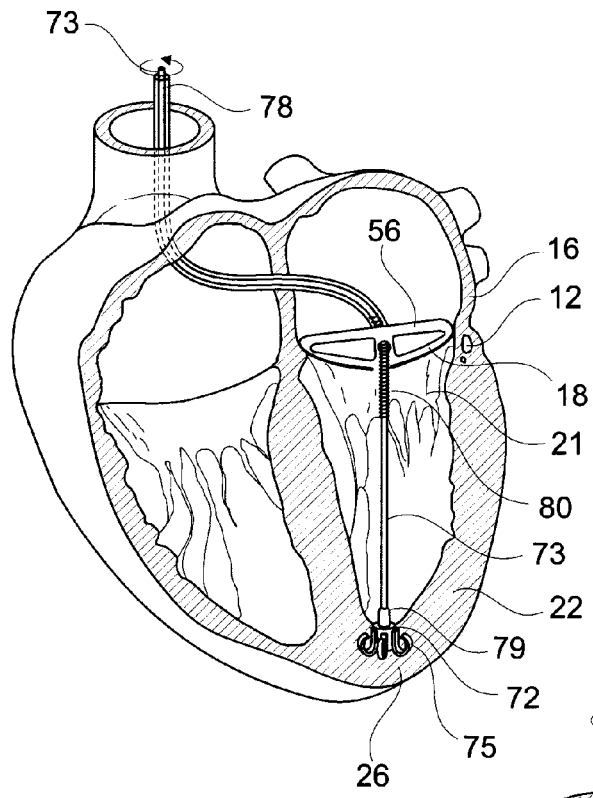
FIGS. 13 *a-b* are schematic illustrations which depict an embodiment using rotational force in order to augment the mitral valve movement.
Figure 13B:
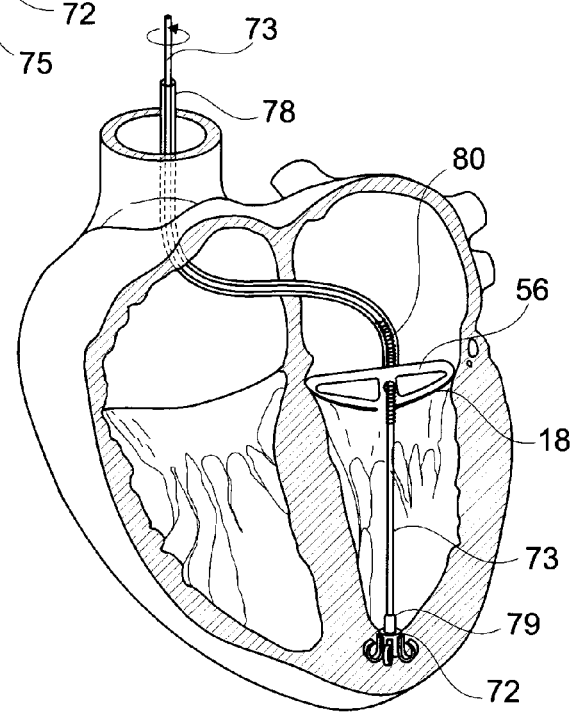

Still another embodiment is now described with reference to FIGS. 13a and 13b. Instead of pulling and pushing the extended extension 73, as described above with reference to FIGS. 10a and 10b, the force is instead transferred by means of rotation of the extension unit 73.

A connection unit 79 to the distal anchor 72 allows the extension 73 to rotate and/or pivot freely relatively to the anchor 72. Such a pivoting connection unit may also be provided in other embodiments having a physical connection between two anchor units, in order to allow for an optimal movement along the LV long axis, which may not entirely be perpendicular to the MV plane. The connection unit 79 may be a swivel joint, e.g. a ball joint type of bearing.

The extension unit 73 is provided with threaded windings 80 in the area of the mitral valve that correspond to mating threaded windings in the mitral valve annulus attachment unit 56. By rotating the extension unit 73 by means of a suitable actuator powered by the remote energy source 84, the mitral valve is forced upwards in diastole as depicted in FIG. 13a. Rotation may be made in counter-clock direction for example. And correspondingly, while rotating the extension unit in the other rotational direction, here clockwise, as shown in FIG. 13b, the mitral valve is in turn forced down along the long axis of the LV towards apex 26, as desired in systole.

Movable units of embodiments, like the threaded windings 80, the pivot joint, etc. may be suitably encapsulated to not be in contact with blood or cardiac tissue to avoid any operational complications. Alternatively, or in addition, moveable units of embodiments may be covered with drugs that prohibit blood components attachment that might compromise proper operation. Examples of such drugs are Heparin or cytostatic drugs like Sirolimus, Tacrolimus or any other drug that would avoid such blood component attachment.

Figure 14:
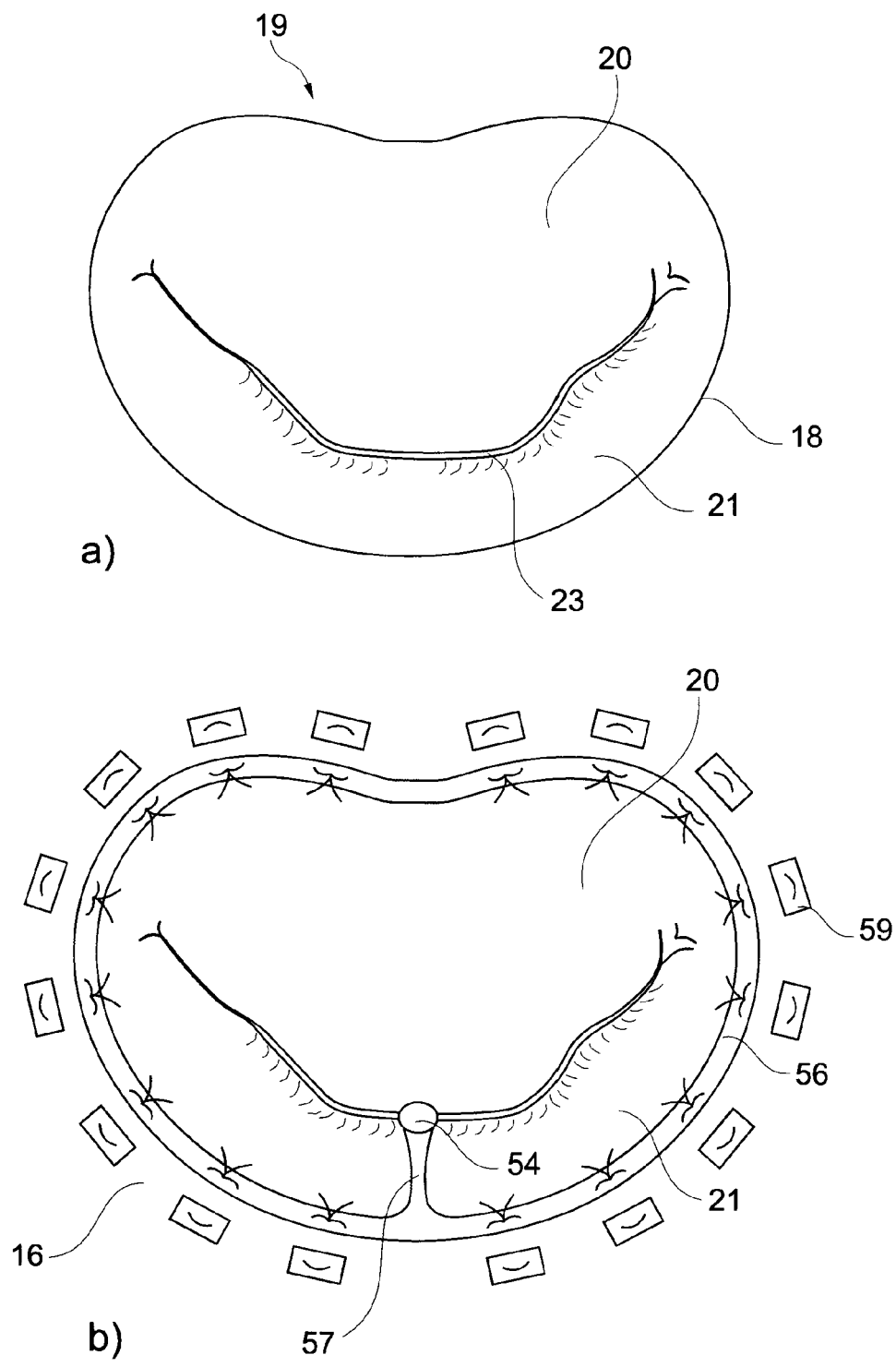
FIGS. 14 *a-b* are schematic illustrations that show a mitral valve and the placement of a mitral valve annulus anchor.

A normal mitral valve is shown in FIG. 14a. The anterior leaflet of the valve 20 is much larger than the posterior leaflet 21. As a result thereof, the coaptation line 23 (line of contact) where the two leaflets meet is not in the centre of the valve but rather posterior. In FIG. 14b, a mitral valve annulus anchor 56 is attached to the annulus by means of sutures 59. The anchor has more or less the native form of the annulus circumference. The pushing and pulling unit 54 and 73 are attached to the anchor by means of an extension unit protruding from the anchor unit 56 towards the coaptation line, like a rod 57. The rod 57 is in this figure shown as being only attached to one position of the anchor 56. The rod 57 may also extend to the other side of the anchor, crossing the entire MV diameter, and be attached here also, as indicated in FIGS. 10, 11 and 13. In the illustrated embodiments the attachment of the pulling and pushing unit 54 and 73 to the mitral valve annulus anchor 56 is made excentric in order to be placed exactly where the coaptation line 23 is. In this manner, the function of the MV is substantially not affected. In other embodiments, the pulling and pushing unit 54 and 73 may also be attached to the anchor 56 itself and penetrate the valve at the annulus, behind preferably the posterior leaflet of the valve.

The MV may be not working properly, e.g. due to insufficient coaptation of the leaflets. In this case, the geometry of the MV may be corrected in order to re-establish correct coaptation and avoid regurgitation. In embodiments, the annulus anchor unit 56 may be provided in form of a loop shaped annuloplasty implant correcting the MV function at the same time as being part of the cardiac assist system, which allows for a synergistic improvement of heart function.

Figure 15:
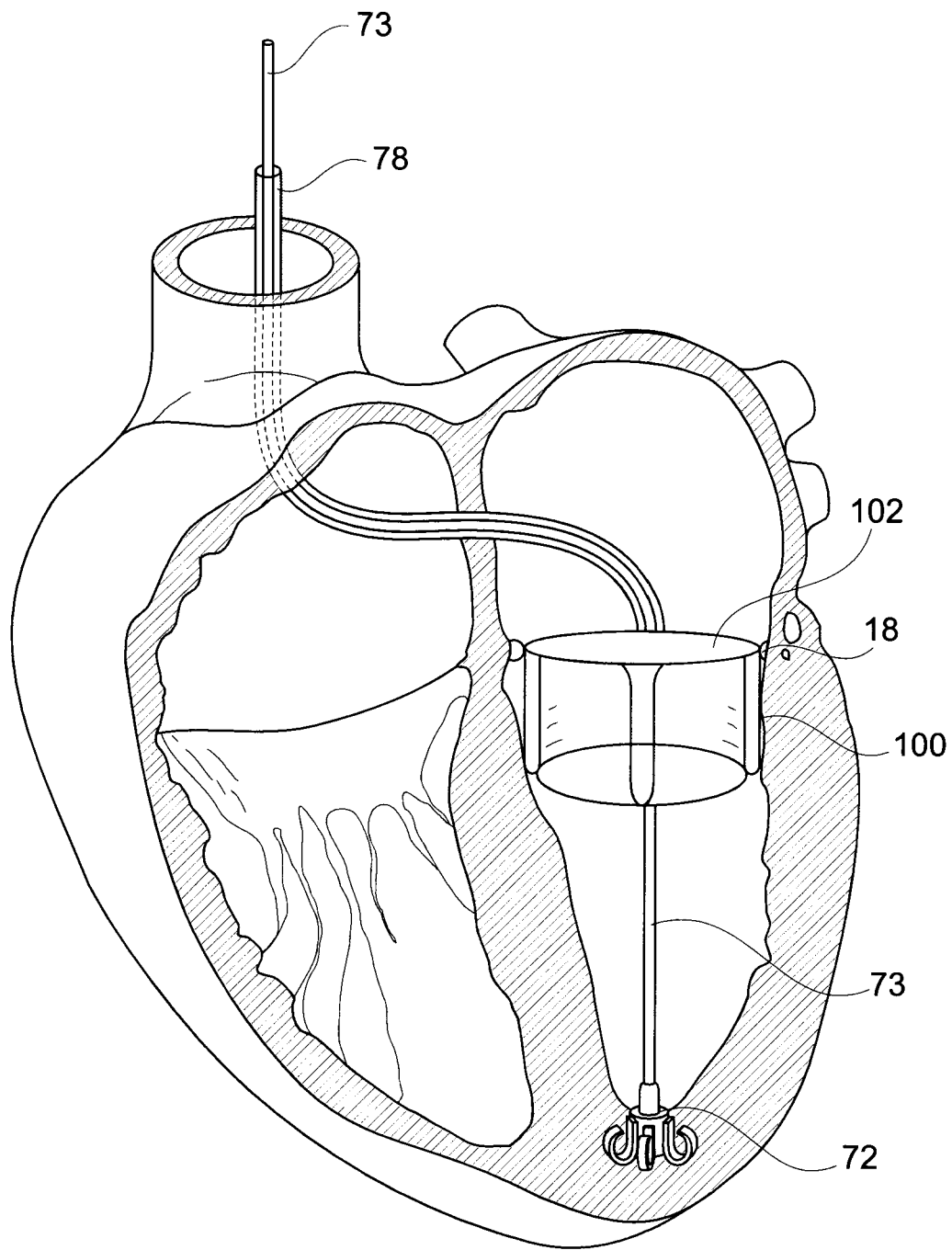
FIG. 15 is a schematic illustration of an artificial heart valve replacing the native mitral valve when integrated in an embodiment of the system.

In situations where the mitral valve is so damaged due to disease that it does not function well, it may be replaced by a replacement artificial valve 100, such as shown in FIG. 15. The native mitral valve has been cut away. Here is a biological replacement valve depicted that is made of bovine pericardium or pig valve tissue treated with Glutaraldehyde. The valve may also be a mechanical artificial replacement heart valve, not shown here. Leaflets 106 (three in the example shown in FIG. 16c) are mounted in a frame or cage. The frame is preferably made of biocompatible material, such as a suitable metal or plastic. The frame is on its exterior affixed to the MV annulus. The frame may conveniently be attached to a suture ring 102. The suture ring 102 is attached to the mitral valve annulus instead of the anchor unit 56, and the pulling and pushing unit 54 and 73 may be attached to the valve frame instead of the anchor unit 56. Cardiac assist function is then provided as in other embodiments by providing a synchronized reciprocating movement of the MV plane of the replacement valve along the LV long axis 49.

Figure 16:
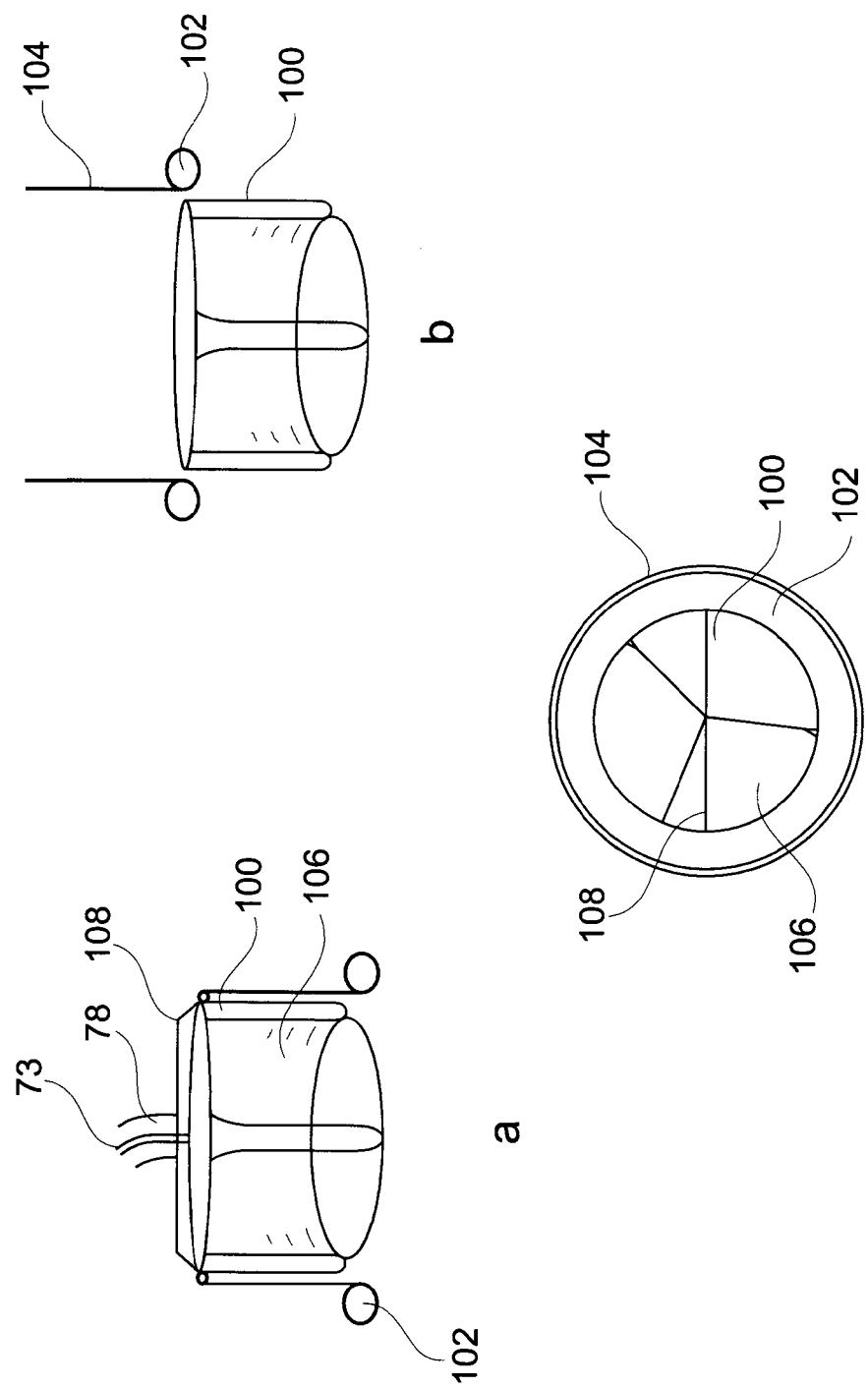
FIGS. 16*a-c* are schematic illustrations of an artificial heart valve in a cage replacing the native heart valve when integrated in an embodiment of the system.
Figure 17:
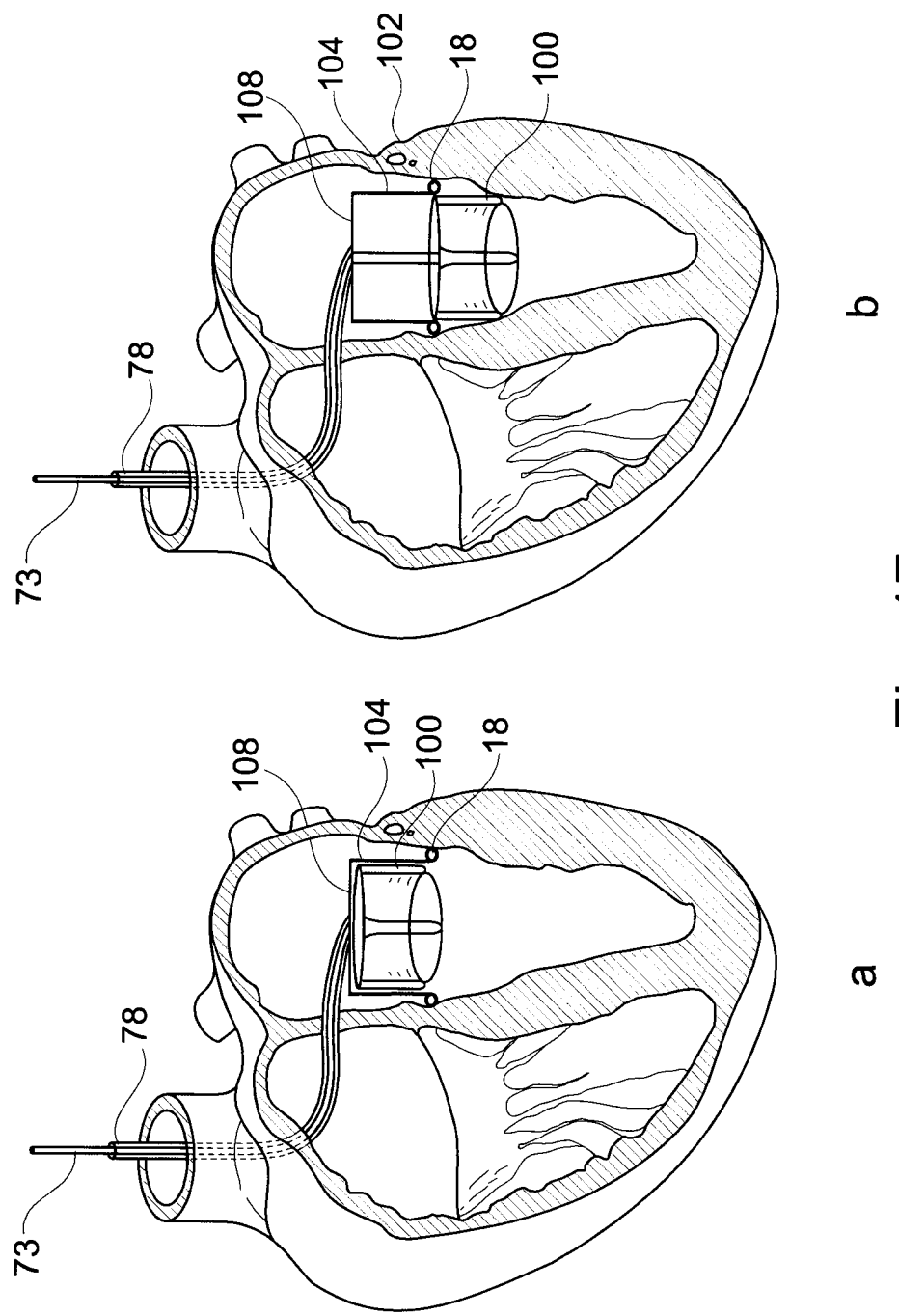
FIGS. 17-19 are schematic illustrations of artificial heart valves when integrated in further embodiments of the innovation.

In still another embodiment, as illustrated in FIGS. 16 and 17, a replacement artificial valve is received in a housing in which the replacement valve is arranged to move in the herein described cardiac assist reciprocating movement along the LV long axis. In the illustrated embodiment, a suture ring 102 is provided to be attached to the mitral valve annulus. A cylinder 104 fits to the size of the suture ring or a sealing ring of the valve allowing the valve to move up and down inside the cylinder, thus acting as a piston. Pushing and pulling unit 54, 73 and 78 may be attached to a cage or struts 108 and to struts integrated in the valve 100. FIG. 17a depicts the valve in an up position during diastole and FIG. 17b in a down position during systole.

Figure 18:
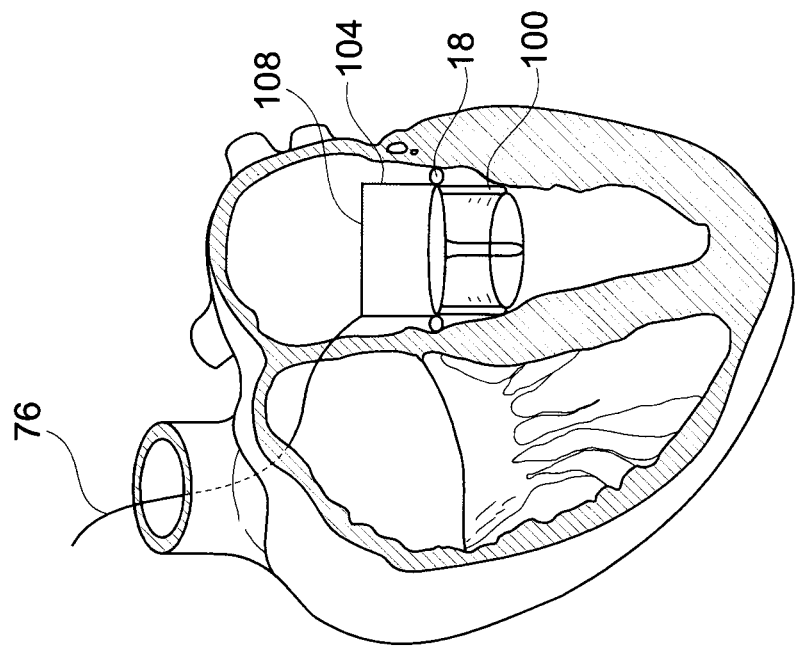

With reference to FIG. 18 a cardiac assist device having a replacement valve is illustrated, where the driving force for the reciprocating synchronized movement is electromagnetic. In the illustrated situation the replacement valve is in the down position in the cage 104. In the example, this is provided by means of two magnets with identical polarity. Opposite polarities moves the valve to the up position. One of the electromagnets may be replaced by a permanent magnet.

Figure 19:
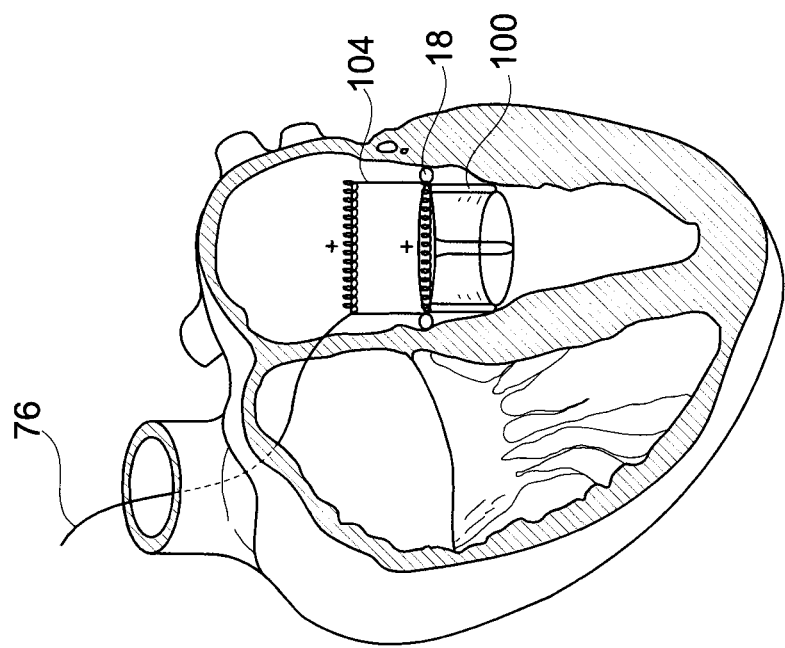

In FIG. 19 it is illustrated that linear actuators or electromotors may also drive the valve up and down in the housing. Such actuators may conveniently be integrated into the components of the replacement valve embodiments. Preferably, the actuators are integrated into the housing with counter elements in the replacement valve.

As can be seen, the replacement valve embodiments do not need a second anchor unit 72. These embodiments are thus advantageous from that point of view. However, a remote second anchor unit 72 may alternatively or in addition be provided in certain embodiments, even with replacement valves, as the skilled person will readily appreciate from the present disclosure.

Figure 20:
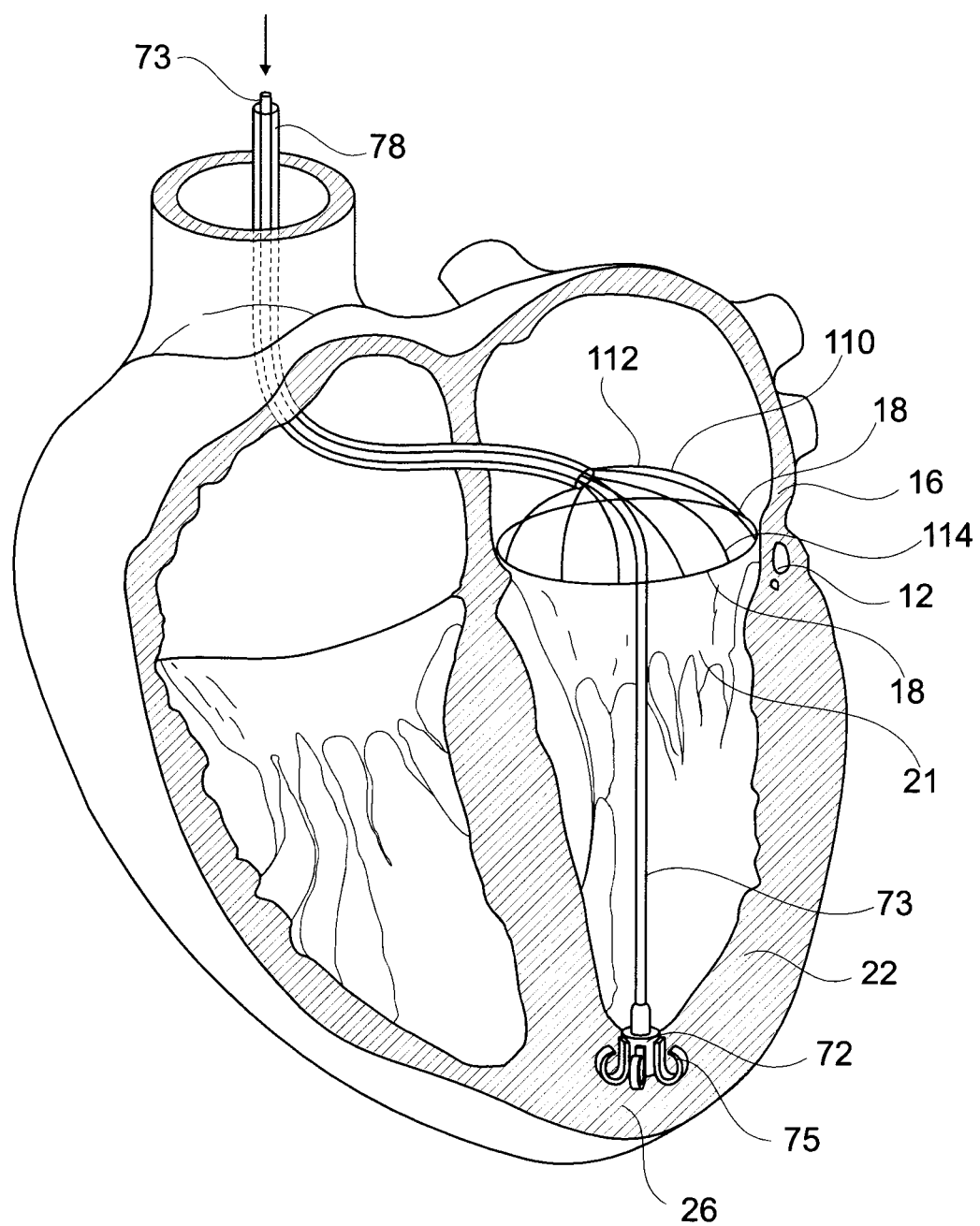
FIG. 20 is a schematic illustrations that depicts an embodiment for complete catheter based implantation of the system.

A complete catheter based version of the cardiac assist system is depicted in FIG. 20. As shown here, the anchor unit 56 is provided in form of a foldable mitral valve annulus anchor 110 that may be retracted inside a catheter while being guided through the vasculature to the mitral valve and to the mitral valve annulus 18 and then unfolded and affixed into place. The foldable anchor may have struts 112 that are attached to the mitral valve annulus, e.g. by means of hooks 114. Such an anchor may also be in the shape of a sling or a foldable ring, not shown. Further minimal invasive embodiments will readily be available to the skilled person by reading the present disclosure and are not depicted in detail, except for further embodiments described below with reference to FIGS. 22 to 30.

In some embodiments the return from the systolic down position of the MV plane to the diastolic up position thereof may be provided at least partly in a passive manner. This may be done in several ways. For instance, the downward supporting action may be stopped pre-mature at the end of systole when there is still sufficient pressure in the LV to press the MV plane back towards the diastole up position. When releasing the supporting force, or a locked position at the end of the systole phase is unlocked, the MV plane is released to move towards the diastole up position. The timing may be cardiac cycle controlled, e.g. based on ECG and/or pressure measurements, in accordance with the description below. Alternatively, or in addition, a return spring element may be provided to support this backwards movement. Alternatively, the systolic position may be spring biased and only the return to the diastolic position has to be made against this spring force by suitable actuators or magnetic energy. Alternatively, or in addition, the cardiac assist system may be provided as a bistable system. Here, the diastolic up position and the systolic down position of the MV plane may be provided as equilibrium states of the system. Energy is provided from the external energy source to initiate the system to move between the two stable positions. These embodiments may be more energy efficient than others.

Permanent magnets in embodiments may be conventional iron magnets. Alternatively, super magnets, like Neodymium rare earth magnets may be used to improve efficiency and/or reduce size of the units of the cardiac assist system, when comprising magnetic elements.

Several actuating principles may be combined with each other in certain embodiments, e.g. a linear actuator and magnetic driving.

Figure 21:
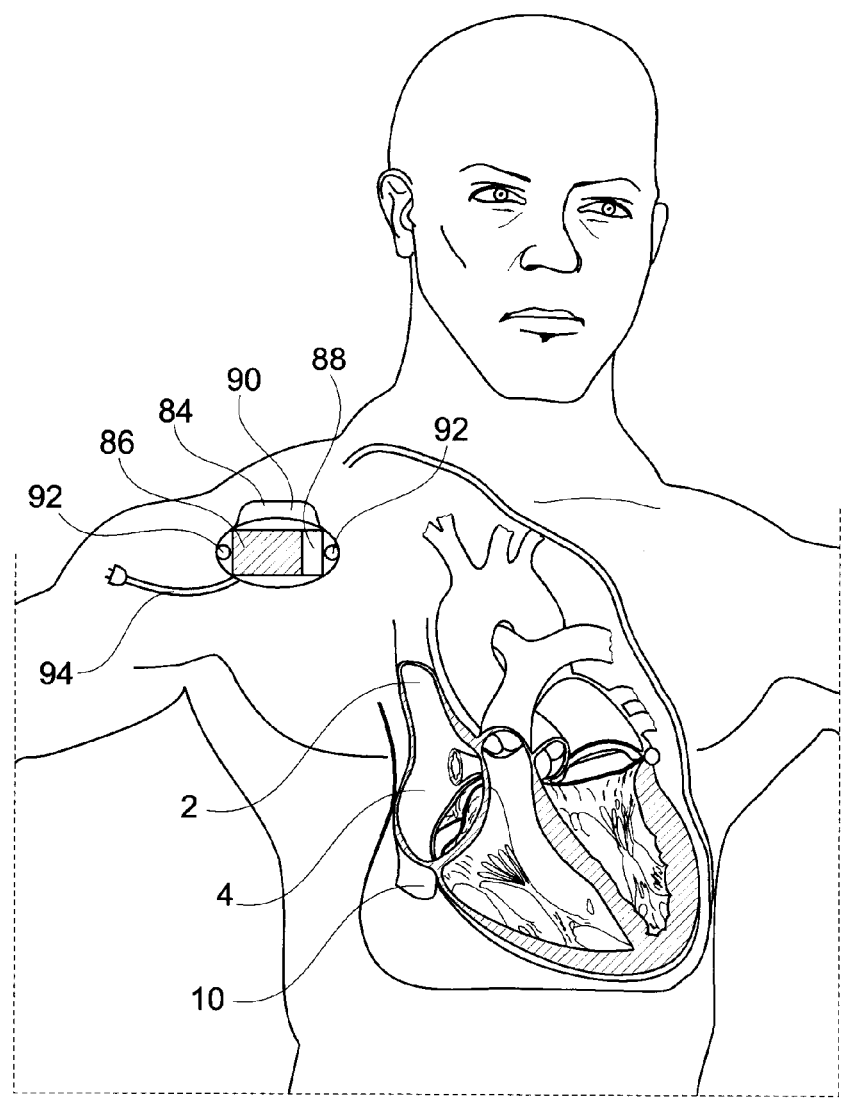
FIG. 21 is a schematic illustration that shows a remote energy source for embodiments.

A remote energy source 84 is shown in FIG. 21. It has a battery section 86 and a computing section 88 containing computer algorithms and chips. The computer section 88 has receiving electrodes or surfaces 92 connected, which are able to detect an Electrocardiogram (ECG) signal. Based on the ECG signal, the cardiac assist device operation is in embodiments controlled in synchronicity with the heart action. Such synchronicity may in addition or alternatively be established by means of detecting other physiological parameters related to the cardiac activity. Such parameters include a blood pressure wave or blood flow patterns.

Alternatively, or in addition, the assisted mitral valve movement may be controlled according to a set sequence of reciprocating movements of the MV plane that mimics the natural cardiac cycle to optimize the cardiac assist function. Frequency, speed, and duration of different pause times of the reciprocating movement may be set in the sequence to mimic a natural or desired movement. The different parameters, such as pause time duration of the movement, may vary over any time interval, and may be set to vary according to a repeating program. The sequence may be programmed into the computing section/control unit 88 which controls the displacement unit. The displacement unit may then provide the assisted movement according to the set sequence. Energy from an energy source 84 may thus be controllably provided to the displacement unit according to the set sequence for providing the assisted movement.

Alternatively, or in addition, the medical device may be incorporated into an artificial pacemaker system controlling or assisting the natural cardiac muscle function. For instance the assisted movement of the cardiac assist device may be controlled from a processing unit of a pacemaker. The pacemaker including the processing unit may be implanted in a patient. The pacemaker triggers heart muscle activity in a per-se known manner, e.g. via leads connected to the cardiac tissue for artificially triggering the cardiac activity. Triggering of the assisted movement of the cardiac assist device may be controlled may be based on the electrical triggering of the cardiac activity by the artificial pacemaker system, which is already synchronized with the cardiac cycle. Preferably a time delay is provided from triggering electrical triggering of the heart muscle activity to the triggering/activation of the assisted movement of the cardiac assist device during a heart cycle. The amount of the time delay may be optimized, depending on the transfer time of electrically triggering the heart muscle activity and the resulting pump function of the heart caused by the controlled heart muscle contraction.

The remote energy source 84 may have a mechanical section 90, where rotational or linear motion may be transferred to extension unit 73. Rotational movement may be transferred directly from an electrical motor, or geared down in revolutions by a gear-box. Rotational energy from an electrical motor may be converted to linear movement, enabling pulling and pushing force to a wire connecting unit 73 that is extending all the way to the distal anchor position. Alternatively, or in addition, the mechanical section 90 may contain other actuators. For instance one or more strong electromagnets may be provided in an actuator that alternately are able to provide pulling and pushing force to a wire connecting unit 73 that is extending all the way to the distal anchor position. Further, the pulling and pushing force from the remote energy source 84 may also be achieved by means of a linear accelerator in the mechanical section 90. Alternatively, or in addition, the mechanical section 90 contains an actuator providing pulling and pushing force to a wire 73 that is extending all the way to the distal anchor position by means of electrically alternately cooling and warming a Nitinol actuator as commercially available from MIGA Motor Company, Modern Motion, www.migamotors.com. Finally, in other embodiments, the remote energy source is without a significant mechanical section, instead computer chips are distributing electricity from the battery according to the detected physiological parameter signal either to electromagnets in one or more of the anchor units of the implanted cardiac assist device or to mini-motors or linear actuators in a heart chamber or on the heart surface as previously described, or to actuators in the housing 104 in FIG. 19, etc.

The remote energy source may have a rechargeable battery that e.g. is charged by means of a wire 94 penetrating the skin and when charging the battery connected to a charging device externally (not shown). Charging might also be done wireless through the skin, e.g. by means of electromagnetic coils transferring energy inductively. The skilled person in the art may alter and design such charging according to specific requirements and available actual technology.

In some particular embodiments, the remote energy source is located in the fatty tissue under the skin, adjacent to a vessel, preferably a large vein. This allows for convenient access to the heart. Alternatively, the energy source may be attached to a bony structure, such as the clavicle (not shown), in order to prohibit dislocation of the same when delivering mechanical energy to the cardiac assist device inside the heart. A pocket 95 in FIG. 28 in the subcutaneous tissue may be created close to the actual vessel, here the subclavian vein 3 in FIG. 28.

A delivery system and a method 800 for complete catheter based insertion of the augmentation system are shown in the FIGS. 22-31.

Figure 22:
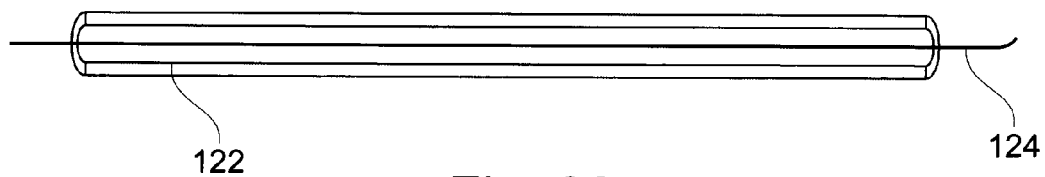

The delivery system has an introducer catheter 120 with a valve, a guiding catheter 122, a guide wire 124 and delivery catheters 126 and 128. FIG. 22 shows the guiding catheter that has a smaller outer diameter than the inner diameter of the introducer catheter to fit inside. By means of the guiding catheter 122 and the guide wire 124 one may navigate through the vasculature and the heart to the desired site for delivering either a distal anchor 72 or a foldable mitral valve annulus anchor 110. All catheters described in the system are made of synthetic material usually used for medical catheters for interventional procedures in the vascular system. Typical such materials are polyvinyl, polychloride, polyethylene, polyurethane and other polymers.

Figure 25:
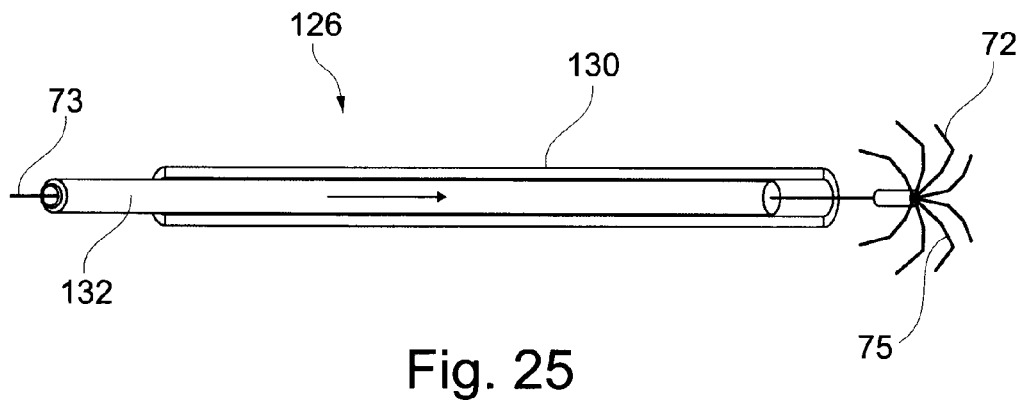

A delivery system for the anchor unit 72 is shown in FIGS. 23-25. FIG. 23 shows a delivery system comprising an outer catheter 130 and a pushing unit 132. The pushing unit 132 is a catheter itself, small enough to fit coaxially inside the outer delivery catheter 130. The pushing unit 132 has a central lumen allowing the pulling and pushing unit 73 to pass there through all the way from outside of a patient and through his or hers vascular system.

The anchor unit 72 is illustrated in FIG. 23 being retracted into the delivery catheter so that the hooks 75 of the anchor are having the tips facing forward towards the catheter opening.

In FIG. 24 two alternative two methods are depicted for navigating the delivery systems 126 and 128. In FIG. 24*a*, the delivery catheter 130 has a smaller outer diameter than the inner diameter of the guiding catheter 122 and may thus travel longitudinally inside the latter. In FIG. 24*b* the delivering of the anchor 72 is made without the guiding catheter 122 in place, instead the delivery system 126 is running over a guide wire 124 previously placed at the delivery site by means of the guiding catheter 122 that subsequently has been retrieved before device insertion. A separate lumen 132 is attached, or integrated with, at least to part of the delivery catheter 130, in other embodiments the guide wire lumen may be inside the delivery catheter (not shown).

In FIG. 25, delivery system 126 for the distal anchor is shown being activated by means of pushing the pushing unit 132 forward while the tip of the delivery catheter has contact with the inner surface of the left ventricle wall 26, allowing the hooks or blades 75 to dig into the muscular tissue.

Figure 26:
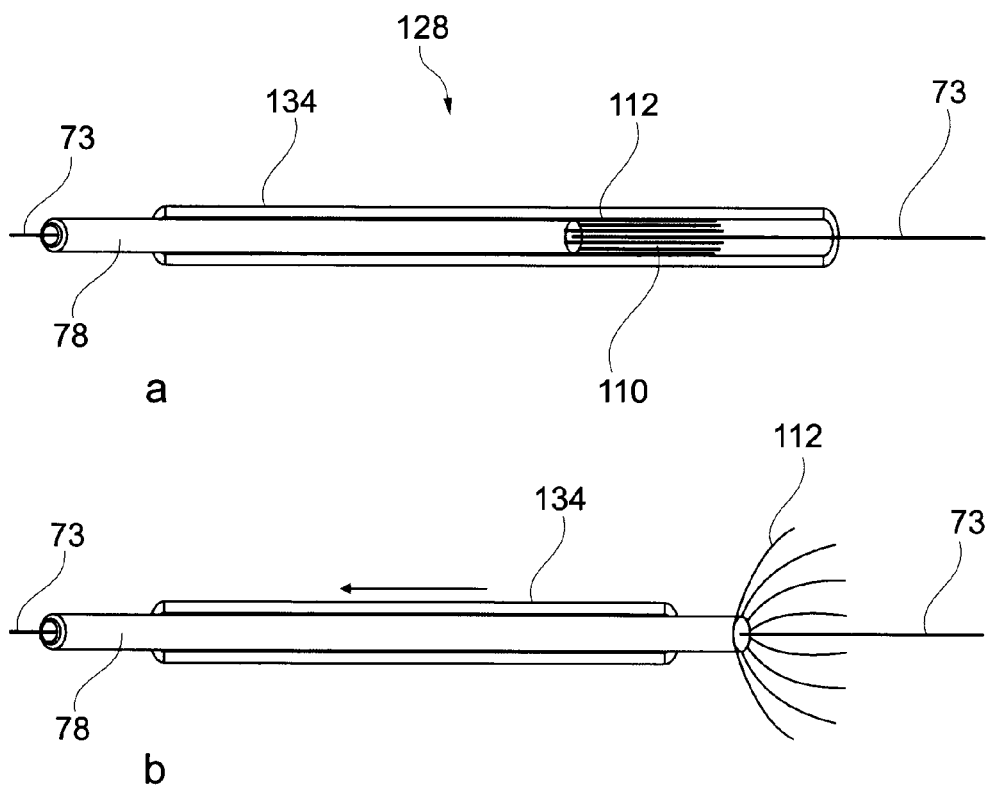
Figure 27:
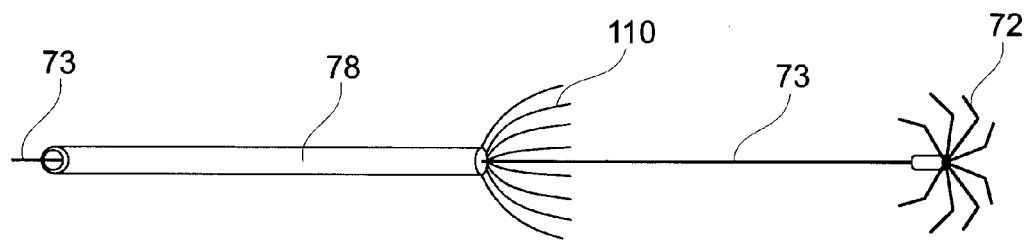

In FIG. 26, a delivery system 128 for the mitral valve annulus anchor 110 is shown. Previously it has been described that the mitral valve annulus anchor 110 is attached to the distal end of catheter 78. The pulling and pushing unit 73 is attached distally to the left ventricular wall by means of anchor 72 and extend through delivery catheter 134 and through the catheter 78 to outside of the patient and its vascular system. The extension 73 is thread through the delivery system 134 by the operator after deployment of distal anchor 72 as described. Releasing the mitral valve annulus anchor 110 is done by retracting the catheter 134 of the delivery system from over the anchor 110 that may attach to the mitral valve annulus 18. FIG. 27 show both anchors 72 and 110 deployed. By pulling or pushing 72 relatively to 110 the mitral valve may be moved up and down relatively to the apex of the heart in synchrony with the cycle of the heart, wherein the movement control is e.g. based on ECG.

Figure 28:
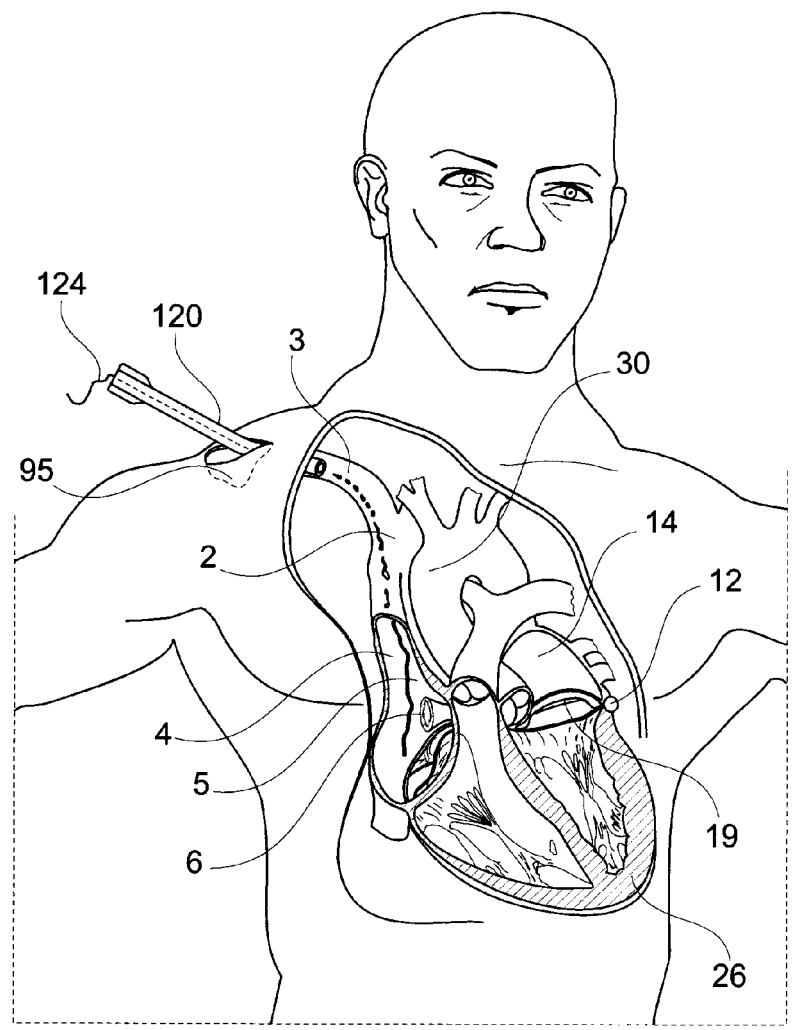
FIGS. 28-30 are schematic illustrations of a method for percutaneous complete catheter based placement of the innovation.
Figure 29:
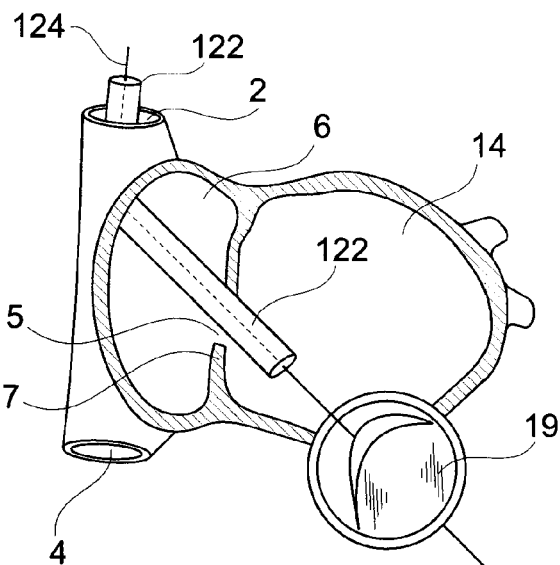
Figure 30:
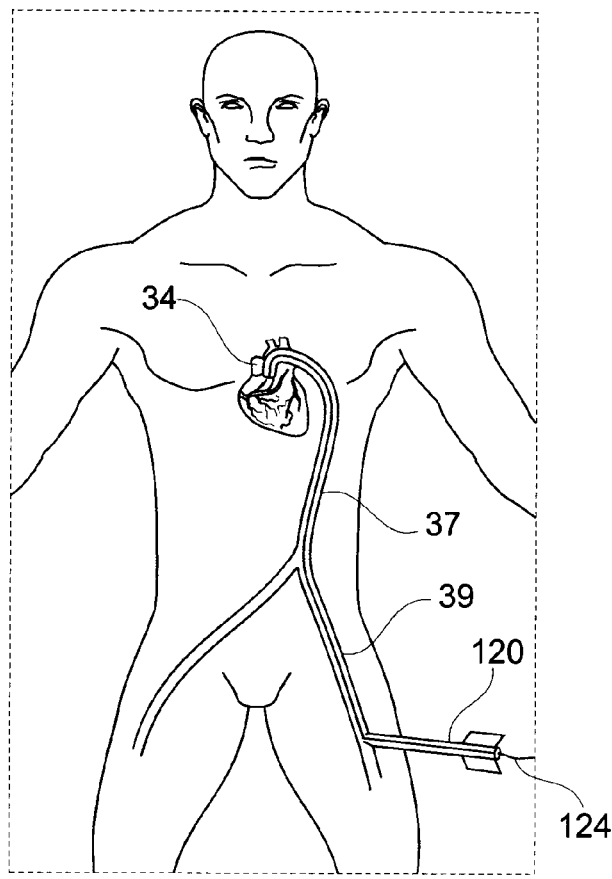
Figure 31:
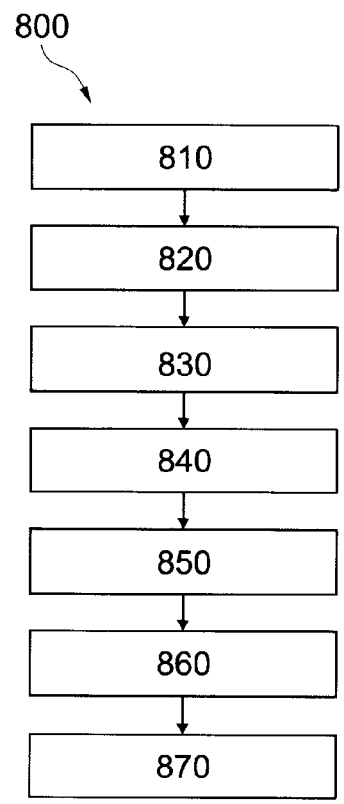
FIG. 31 is a flowchart of the method.

A method for permanently augmenting the heart pumping function by means of assisted mitral valve movement based on complete catheter based technology is described with reference to FIGS. 28-31. FIG. 28 shows the heart and the great vessels of a human being, and FIG. 29 the right and left atrium, the atrial septum 7, foramen ovale 5 and the mitral valve 19. Preferably access to the vascular system is made in step 810 by puncturing a large vein, shown here is the subclavian vein 3, but any other large vein might be used, for instance the femoral vein in the groin. An alternative, is a route through the arterial system for access is depicted in FIGS. 30, 39 is the iliac or femoral artery and 37 the abdominal and thoracic aorta. Only the vein access will be described here: An introducing large catheter 120 with a valve (in order to prohibit blood spill) is placed in the vein. Through the introducer catheter a guide wire 124 is advanced, and over the guide wire a guide catheter is advanced in step 820 to the right atrium 4. From here access is obtained to the left atrium 14 either by penetrating an open foramen ovale (a native opening between the two atria), or by means of pushing a needle (not shown) through the inter-atrial wall 7 and thereafter advancing the guiding catheter over the needle extension into the left atrium 14. Further, the guide catheter 122 and the guide wire 124 are advanced into the left ventricle through the mitral valve 19. Once the guide catheter has contact with the left ventricular muscular wall at the desired site, the delivery system 126 for the anchor 72 is advanced inside the guide catheter or over a guide wire 124 in step 830 until its catheter opening has contact with the inner surface of the left ventricular wall 26. By means of advancing the pushing catheter 132, the tips of the hooks or blades 75 of anchor 72 will dig into the muscular tissue and pull the anchor inside the musculature an thereby create an secure anchoring of the pulling and pushing unit 73. The inventor has on several occasions placed such anchors into the left ventricular musculature in animal experiences and observed the hooks pull themselves into the tissue. In one embodiment of the method, the anchor is allowed to heal into the musculature by scar tissue over a period of preferably 6-12 weeks before the cardiac assist system is activated. In animal experiments the inventor has found such scar attachment stronger than the musculature itself, and by pulling 1.5 to 2 kilogram force was necessary to pull the anchor out, and then only together with the scar tissue.

Once the anchor has been deployed, catheters 130 and 132 are retracted from the patient over the pulling and pushing unit 73. Now the delivery system 128 for the mitral valve annulus anchor 110 is advanced over the pulling and pushing unit 73 in step 840 until the anchor 110 and its arms 112 are adjacent to the mitral valve annulus. When in position, the catheter 134 is retracted over the catheter 78 until outside of the patient. The arms 112 and their attachments hooks 114 are allowed to attach to the mitral valve annulus and dig into the tissue in step 850. Again the same healing in period of preferably 6-12 weeks before activation of the system as already described may be applied. Other foldable slings or rings may be used instead the arms described of anchor 110. A person skilled in the art of catheter based technologies may use other methods for attachments, still being within the scope of this innovation. Once both anchors 72 and 110 are securely attached, the pushing and pulling unit 73 and the catheter 78 are adjusted in length and attached to the remote energy source 84 in step 860, and the system may be activated in step 870. The remote energy source has a unit to detect the natural action of a heart, e.g. based on an electrocardiogram, a blood pressure wave or blood flow. The remote energy source may thus provide energy for the distance change between the two anchors in synchrony with the natural heart cycle, thereby enhancing the natural up and down movement of a mitral valve during a heart cycle.

A surgical method for permanently augmenting the heart pumping function by means of assisted mitral valve movement based on surgical technology is described with reference to FIGS. 10-19 and 21. Surgical access to the mitral valve, the mitral valve annulus and the left ventricle is achieved by means of surgically opening the chest of a human being and establishing extra corporeal circulation (ECC) using a heart- and lung machine (HLM). One anchor unit is attached in the area of the left ventricular apex, in the musculature, on the left ventricular apex outside or in adjacent tissue. A second anchor unit is attached to the mitral valve annulus, preferably by means of suturing, but also clips or hooks or other suitable methods for attachment may be used. The two anchors are connected to each other by means of connecting unit that may shorten and increase the length between the anchors. The connecting unit is attached to a remote energy source. The remote energy source has means to detect the natural action of a heart e.g. in the form of an electrocardiogram, a blood pressure wave or blood flow. The remote energy source may thus provide energy for the distance change between the two anchors in synchrony with the natural heart cycle, thereby enhancing the natural up and down movement of a mitral valve during a heart cycle. Analog to the here described surgical method, one magnetic anchor may be attached to the mitral valve annulus in a similar way, while a second magnetic anchor is attached to left ventricular musculature or elsewhere in the heart, or adjacent to the heart as described above. The remote energy source has means to detect the natural action of a heart e.g. in the form of an electrocardiogram, a blood pressure wave or blood flow. The remote energy source may thus provide electrical energy through leads to the magnets in order to charge the magnets and change the polarity of the magnets, thereby providing energy for the distance change between the two magnetic anchors in synchrony with the natural heart cycle, thereby enhancing the natural up and down movement of a mitral valve towards and away from the apex of the heart during a heart cycle.

In another embodiment of a surgical method, the native heart valve is replaced by an artificial valve serving as both the mitral valve and the mitral annulus anchor.

In still another surgical method for using the invention, an artificial heart valve is mounted in a cage or housing, allowing the heart valve to move up and down relatively to the mitral valve annulus attachment by means of the remote energy source as described.

Finally in a further embodiment of the surgical method, access to the heart is achieved by surgically opening the chest. Without the use of ECC the device insertion to the heart structures is done by means of manipulating the heart manually from the outside, while still pumping.

A concurrently filed patent application titled "A DEVICE, A KIT AND A METHOD FOR HEART SUPPORT" with Application Serial No. PCT/SE2011/050337 and Publication No. WO 2011/119100 claiming priority to U.S. Provisional Application Ser. No. 61/317,619 filed Mar. 25, 2010, and Swedish application Serial No. SE1050282-1 filed Mar. 25, 2010 with Publication No. SE 535690, both entitled "Device, a Kit and a Method for Heart Support", of the same applicant as the present application, which are all incorporated herein by reference in their entirety for all purposes. This co-pending application discloses devices and methods for permanently augmenting the pump function of the left heart. The mitral valve plane is assisted in a movement along the left ventricular long axis during each heart cycle. The very close relationship between the coronary sinus and the mitral valve is used by various embodiments of a medical device providing this assisted movement. By means of catheter technique an implant is inserted into the coronary sinus (CS), the device is augmenting the up and down movement of the mitral valve and thereby increasing the left ventricular diastolic filling and the piston effect of the closed mitral valve when moving downwards for augmenting the left ventricular pumping effect. Embodiments of the present disclosure may be combined with embodiments of the co-pending application. For instance an annuloplasty ring may be provided as a mitral valve intra-atrial or intra-ventricular anchor unit with a CS anchor unit or driving unit as described in the co-pending application. A prosthetic artificial MV may be provided in combination with CS anchor unit or driving unit, etc. The MV plane may advantageously be mechanically stabilized and moved more efficiently by some of these combined embodiments.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

As used herein and in the claims below, "displacement means" comprises a linear actuator connected by an anchor attached to the mitral valve. The linear actuator is additionally secured either directly or indirectly to the apex of the heart and is power by a motor connected to a remote or external power source to causes a push and/or pull reciprocating movement of the mitral valve. Alternatively the "displacement means" comprises two magnetic anchors, a first one of the magnetic anchors mounted at the mitral valve and the second one of the magnetic anchors mounted remotely. The second magnetic anchor comprises an electromagnet powered to alternatively attract and repel the first magnetic anchor, thereby changing the distance between the magnetic anchors, creating the reciprocating movement of the mitral valve.

The invention claimed is:

1. A medical device adapted to enhance intra-cardiac blood circulation of a heart of a patient by assisting left ventricular pump action, said device having a displacement means for controllably assisting movement of a mitral valve in a mitral valve plane substantially along a long axis of a left ventricle of said heart, and said displacement means configured to be arranged in said heart of said patient in contact with said mitral valve to push and/or pull said mitral valve such that said mitral valve moves in a reciprocating movement that is assisted during systole along said long axis towards an apex of said heart and/or during diastole along said long axis away from said apex for assisting said pump action of said heart.

2. The device of claim 1, wherein said displacement unit comprises a mechanical unit devised to apply a mechanical supporting force to the mitral valve during at least a portion of systole for augmenting the natural pumping force of the heart, and/or during at least a portion of diastole for augmenting a natural filling of the left ventricle.

3. The device of claim 2, wherein said mechanical unit has a proximal end portion that is configured to be attached to a location on the mitral valve and wherein said medical device further comprises an energy converter unit attached to a distal end portion of said mechanical unit that transfers energy from a remote energy source into a linear force and/or a rotational force for providing said supporting force.

4. The device of claim 3, wherein said proximal end portion is configured to be attached to the mitral valve annulus by means of a fixation unit.

5. The device of claim 4, wherein said fixation unit is at least partly loop shaped and adapted to be affixed to the mitral valve annulus and has an extension unit protruding from said fixation unit towards a coaptation line of said mitral valve, and wherein said mechanical unit is configured to be attached to said fixation unit at said extension unit at said coaptation line.

6. The device of claim 4, wherein said fixation unit is at least partly loop shaped and adapted to be affixed to the mitral valve annulus, and wherein said mechanical unit is attached to said fixation unit at a circumference of said fixation unit, wherein said mechanical unit is adapted to penetrate said mitral valve at the mitral valve annulus, preferably behind a posterior leaflet of the mitral valve.

7. The device of claim 1, wherein said displacement unit comprises a magnetic unit devised to apply a magnetic supporting force to the mitral valve during at least a portion of systole for augmenting the natural force of the heart, and/or during at least a portion of diastole for augmenting a natural filling of the left ventricle.

8. The device of claim 7, wherein a first anchor unit of said magnetic unit is an electromagnet that is configured to controllably change polarity synchronously with the heart cycle.

9. The device of claim 1, wherein said displacement unit comprises a plurality of magnetic tissue anchors, including a first, proximal magnetic anchor and a second, distal magnetic anchor, which are controllably and selectively magnetic relative each other, wherein said first anchor is configured to be located at the mitral valve, and the second anchor is configured to be located remote from the first anchor inside or outside said heart.

10. The device of claim 9, wherein one of said magnetic anchors is a loop shaped annuloplasty implant.

11. The device of claim 9, wherein said second anchor is adapted to be located in an atrial or ventricular septum, wherein the second anchor is adapted to be inserted into and occlude an opening in said atrial or ventricular septum.

12. The device of claim 9, wherein said second anchor is adapted to be located in the left atrial appendage (LAA), wherein the second anchor is an LAA occluder.

13. The device of claim 1, further comprising an energy source, wherein said displacement unit is arranged to be driven by energy from said energy source, and wherein said energy source is adapted to provide said energy to push and/or pull said mitral valve.

14. The device of claim 13, wherein said energy is movement energy that is mechanically transferred from said energy source through an extended connecting unit to said displacement unit.

15. The device of claim 13, wherein said displacement unit comprises an actuator, and said energy is electrical energy that is electrically transferred from said energy source to said actuator.

16. The device of claim 1, wherein said mitral valve is a native mitral valve and said displacement unit is configured to be affixed in relation to said mitral valve to controllably assist movement of the mitral valve along the long axis of the left ventricle towards and/or away from the heart apex in synchrony with the cardiac cycle.

17. The device of claim 1, wherein the device comprises an artificial valve and said artificial valve comprises a hollow frame having a longitudinal extension, wherein said frame is configured to be oriented in said h art perpendicular to said mitral valve plane and to be affixed to a mitral valve annulus, and wherein said frame is connected to said displacement unit.

18. The device of claim 17, wherein said displacement unit comprises a housing in which said artificial valve is movably received, said housing having a longitudinal extension configured to be oriented in said heart perpendicular to the mitral valve plane and configured to be affixed to the mitral valve annulus at a mitral valve annulus attachment in said housing, wherein said replacement valve is arranged to move along the left ventricular long axis relative to said mitral valve annulus attachment in said housing.

19. The device of claim 1, wherein the displacement means comprises an anchor in the form of a foldable mitral valve annulus anchor unit affixable to a mitral valve annulus.

20. The device of claim 1, wherein said displacement unit is bistable between a stable diastolic up position and a stable systolic down position of the mitral valve plane, wherein said displacement unit has equilibrium states in the up and down position respectively, and wherein the displacement unit moves between the two stable positions when energy from an external energy source is controllably provided to the displacement unit in synchrony with the cardiac cycle.

21. The device of claim 1, wherein said device has a remote energy source, a control unit, and a sensor operatively connected to said control unit for measuring physiological parameters related to a cardiac cycle activity providing a sensor signal, wherein said sensor signal is provided to said control unit which controls said displacement unit to controllably assist movement of said mitral valve by energy from said remote energy source and based on said sensor signal.

22. The device of claim 21, wherein said remote energy source has a mechanical section and an extension unit devised to be arranged between said mechanical section and said displacement unit, wherein mechanical motion is generated by said mechanical section in operation thereof and transferred to said displacement unit to controllably assist movement of said mitral valve via said extension unit.

23. The device of claim 21, wherein said remote energy source is controlled by said control unit to provide electrical energy to one or more electromagnetical anchor units configured to be affixed in relation to said mitral valve, or to at least one actuator configured to be arranged at or in the heart, to contollably assist movement of said mitral valve.

24. The device of claim 21, wherein said remote energy source is adapted to be located in fatty tissue adjacent to a large vein.

25. The device of claim 1, wherein said device comprises a control unit which controls said displacement unit to controllably push and/or pull said mitral valve in a set sequence.

26. The device of claim 25, wherein said control unit is configured to set a frequency, and/or a speed, and/or a pause time duration of said set sequence.

27. A kit comprising the device of claim 1, and a delivery system for said device, including an introducer catheter with a valve, a guiding catheter, a guide wire and at least one delivery catheter.

28. A medical method of delivering a medical device adapted to enhance intra-cardiac blood circulation of a heart of a patient by assisting left ventricular pump action, said medical device having a displacement means for controllably moving a mitral valve in a mitral valve plane substantially along a long axis of a left ventricle of said heart, and said displacement means being configured to be arranged in said heart of said patient in contact with said mitral valve to push and/or pull said mitral valve such that said mitral valve is moved in a reciprocating movement that is assisted during systole towards an apex of said heart and/or during diastole away from said apex for assisting said pump action of said heart, said method comprising providing a medical system including said medical device and an energy source, and surgically and/or minimally invasively delivering said medical system in said patient.

29. The method of claim 28, wherein said method comprises providing a delivery system according to claim 27, for minimally invasively delivering said medical device in said patient, and minimally invasively delivering said displacement unit of said medical system in said patient by means of said delivery system, delivering said energy source, and connecting said energy source and said displacement unit.

30. The method of claim 29, wherein said delivery system includes an introducer catheter with a valve, a guiding catheter and a guide wire, and wherein said method comprises introducing said introducer catheter at a puncture site into the vascular system of said patient, inserting said guide wire into said vascular system via said introducer catheter, navigating through the vasculature and the heart to a desired site, inserting said guiding catheter over said guide wire, withdrawing said guide wire, through said guide catheter delivering a first anchor unit at a distance from a mitral valve and delivering a second anchor unit at said mitral valve.

31. The method of claim 29, wherein said delivery system includes an introducer catheter with a valve, a delivery catheter and a pushing unit, a guide wire and a guiding catheter, wherein said method comprises introducing said introducer catheter at a puncture site into the vascular system of said patient, inserting said guide wire into said vascular system via said introducer catheter, navigating through the vasculature and the heart to a delivery site, inserting said guide catheter over said guide wire, providing an anchor unit at a distal end of said pushing unit, introducing said distal end in front of said pushing unit into said delivery catheter, and a) wherein said delivery catheter has a smaller outer diameter than an inner diameter of the guiding catheter, and longitudinally moving the delivery catheter in said guide catheter, or b) retracting said guide catheter, and longitudinally moving the delivery catheter over said guide wire previously placed at the delivery site by means of the guide catheter; and activating said anchor unit by means of pushing said pushing unit forward while the tip of the delivery catheter has contact with the surface of the delivery site and allowing anchor elements of the anchor unit to dig into tissue at said delivery site.

32. The method of claim 31, comprising threading an extension unit through said delivery system and releasing a mitral valve annulus anchor by retracting the catheter of the delivery system from over the mitral valve annulus anchor, and attaching the mitral valve annulus anchor to a mitral valve annulus.

33. The method of claim 28, comprising providing access to a vascular system by puncturing a large vein, placing an introducer catheter with a valve in the vein, through the introducer catheter advancing a guide wire, and over the guide wire advancing a guide catheter to a right atrium, obtaining access to a left atrium by penetrating through an open foramen ovale or through an inter-atrial wall and thereafter advancing the guide catheter into the left atrium, and advancing said guide catheter and the guide wire into the left ventricle through the mitral valve to a delivery site at a left ventricular wall;

advancing a delivery system for an anchor unit inside the guide catheter or over a guide wire until contact is made with an inner surface of the left ventricular wall, advancing a pushing catheter and pushing said anchor unit out of the guide catheter opening to dig into a muscular tissue and pull the anchor unit inside said muscular tissue, and thereby creating a secure anchoring of a pulling and/or pushing unit, and retracting the delivery catheter and pushing unit.

34. The method of claim 33, comprising advancing a delivery system for a mitral valve annulus anchor over the pulling and/or pushing unit until the anchor and its arms are adjacent to a mitral valve annulus, and when in position, retracting the quide catheter over the pushing catheter until outside of the patient, allowing arms and their attachments hooks to attach to the mitral valve annulus and dig into tissue.

35. The method of claim 34, adjusting the pulling and/or pushing unit and the catheter in length and attaching these to the energy source.

36. The method of claim 34, comprising positioning said energy source in fatty tissue, adjacent to a large vein, and attaching the energy source to a bony structure.

37. The method of claim 28, wherein said method comprises providing surgical access to the mitral valve, a mitral valve annulus and the left ventricle including surgically opening a chest of a human being and establishing extra corporeal circulation (ECC) or manipulating the heart manually while still pumping.

38. The method of claim 37, said method comprising activating said medical device for controllably assisting movement of the mitral valve in the mitral valve plane substantially along the long axis of the left ventricle of said heart by said displacement unit, wherein said controllably moving comprises moving a mitral valve in said heart in a reciprocating movement that is assisted during systole towards an apex of said heart and/or during diastole away from said apex for assisting said pump action of said heart.

39. The method of claim 28, comprising
attaching a first anchor unit in a musculature inside a left ventricular apex, or outside on the left ventricular apex, or in adjacent tissue,
attaching a second anchor unit to a mitral valve annulus, and either
connecting said first and second anchors to each other by means of a connecting unit that may shorten and increase a length between the anchors, and attaching the connecting unit to a remote energy source or
replacing the mitral valve by an artificial valve serving as both the mitral valve and the second anchor unit.

40. A system for permanently enhancing left ventricular pump function of a heart of a patient, said system comprising a displacement means for controllably assisting mitral valve movement synchronized with a cardiac cycle of said heart substantially along a long axis of a left ventricle of said heart, said displacement means being configured to be arranged in said heart of said patient in contact with said mitral valve to push and/or pull said mitral valve such that said mitral valve moves in a reciprocating movement that is assisted during systole towards an apex of said heart and/or during diastole away from said apex for assisting pump action of said heart.

* * * * *